(12) United States Patent
Wang et al.

(10) Patent No.: US 9,222,856 B2
(45) Date of Patent: Dec. 29, 2015

(54) MEASUREMENT OF PARTICLE MORPHOLOGY USING FILTRATION

(71) Applicant: REGENTS OF THE UNIVERSITY OF MINNESOTA, Minneapolis, MN (US)

(72) Inventors: Jing Wang, Zurich (CH); David Y. H. Pui, Plymouth, MN (US); Heinz Fissan, Kerken (DE); Sheng-Chieh Chen, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 250 days.

(21) Appl. No.: 13/779,308

(22) Filed: Feb. 27, 2013

(65) Prior Publication Data

US 2013/0174643 A1    Jul. 11, 2013

Related U.S. Application Data

(63) Continuation-in-part of application No. PCT/US2011/049340, filed on Aug. 26, 2011.

(60) Provisional application No. 61/377,550, filed on Aug. 27, 2010.

(51) Int. Cl.
*G01N 15/00* (2006.01)
*G01N 1/28* (2006.01)
(Continued)

(52) U.S. Cl.
CPC .............. *G01N 1/28* (2013.01); *G01N 15/0272* (2013.01); *G01N 15/06* (2013.01); *G01N 2015/0065* (2013.01)

(58) Field of Classification Search
CPC .............................................. G01N 2015/0662
USPC ........................................................ 73/28.04
See application file for complete search history.

(56) References Cited

U.S. PATENT DOCUMENTS 4,786,473 A * 11/1988 Mukogawa et al. ......... 73/61.73
4,790,650 A   12/1988 Keady
5,302,354 A *  4/1994 Watvedt et al. .............. 422/177

(Continued)

FOREIGN PATENT DOCUMENTS

DE    198 46 656 A1    4/1999
GB    2 346 700 A       8/2000

(Continued)

OTHER PUBLICATIONS

Brown, *Air Filtrations: An Integrated Approach to the Theory and Applications of Fibrous Filters*, Pergamon, Oxford, U.K., 1993.

(Continued)

*Primary Examiner* — Laura Martin
*Assistant Examiner* — Alex Devito
(74) *Attorney, Agent, or Firm* — Mueting, Raasch & Gebhardt, P.A.

(57) ABSTRACT

A system and method for characterizing a totality of particles selects a class of the totality of particles having a defined mobility; determines the total particle concentration of the class of particles; filters the class of particles using the filter apparatus and determines a filtered particle concentration indicative of the particles of the class which penetrate the filter apparatus; and determines at least one morphological parameter based on the fraction of particles of a class penetrating the filter apparatus.

20 Claims, 12 Drawing Sheets

(51) Int. Cl.
*G01N 15/02* (2006.01)
*G01N 15/06* (2006.01)

(56) References Cited

U.S. PATENT DOCUMENTS

| | | | |
|---|---|---|---|
| 5,973,904 | A | 10/1999 | Pui et al. |
| 6,145,391 | A | 11/2000 | Pui et al. |
| 7,105,042 | B2 | 9/2006 | Tumbrink et al. |
| 2004/0080321 | A1 | 4/2004 | Reavell et al. |
| 2006/0284077 | A1 | 12/2006 | Fissan et al. |
| 2009/0056535 | A1 | 3/2009 | Moosmuller et al. |
| 2009/0134322 | A1 | 5/2009 | Thomson |
| 2010/0096547 | A1 | 4/2010 | Allmaier et al. |

FOREIGN PATENT DOCUMENTS

| | | |
|---|---|---|
| GB | 2 374 671 A | 10/2002 |
| GB | 2 378 510 A | 2/2003 |
| JP | 2007127427 A | 5/2007 |
| WO | 91/08459 | 6/1991 |
| WO | 99/41585 | 8/1999 |
| WO | 00/78447 A1 | 12/2000 |
| WO | 2004/009243 A1 | 1/2004 |
| WO | 2005/039780 A2 | 5/2005 |
| WO | 2007/000710 A2 | 1/2007 |
| WO | 2007/016711 A1 | 2/2007 |
| WO | 2009/098215 A1 | 8/2009 |
| WO | 2012/027665 A1 | 3/2012 |

OTHER PUBLICATIONS

Hinds, *Aerosol technology: Properties, behaviour, and measurement of airborne particles*, Second ed., Wiley-Interscience, New York, USA, 1999.

International Preliminary Report on Patentability mailed Mar. 5, 2013, for International Application No. PCT/US2011/049340, filed Aug. 26, 2011; 5 pgs.

International Search Report mailed Jan. 10, 2012, for International Application No. PCT/US2011/049340, filed Aug. 26, 2011; 2 pgs.

Kim et al., "Structural Property Effect of Nanoparticle Agglomerates on Particle Penetration through Fibrous Filter," *Aerosol Sci. & Technology*, 2009; 43:344-355.

Lall et al., "On-line measurement of ultrafine aggregate surface area and volume distributions by electrical mobility analysis: I. Theoretical analysis," *Aerosol Science*, 2006; 37:260-271.

Lall et al., "On-line measurement of ultrafine aggregate surface area and volume distributions by electrical mobility analysis: II. Comparisons of measurement and theory," *Aerosol Science*, 2006; 37:272-282.

Lange et al., "Predicting the Collection Efficiency of Agglomerates in Fibrous Filter," *Particle & Particle Systems Characterization*, 1999; 16:60-65.

Manton, "The impaction of aerosols on a nuclepore filter," *Atmospheric Environment*, 1978; 12:1669-1675.

Manton, "Brownian diffusion of aerosols to the face of a Nuclepore filter," *Atmospheric Environment*, 1979; 13:525-531.

Spurny et al., "Aerosol filtration by means of nuclepore filters: Structural and Filtration properties," *Environmental Science and Technology*, 1969; 3:453-464.

Written Opinion mailed Jan. 10, 2012, for International Application No. PCT/US2011/049340, filed Aug. 26, 2011; 4 pgs.

Vainshtein et al., "Mobility of permeable fractal agglomerates in slip regime," *J. Colloid Interface Sci.*, 2005; 284:501-509.

Wang et al., "Filtration of aerosol particles by elliptical fibers: a numerical study," *Journal of Nanoparticle Research*, 2009; 11:185-196.

Wang et al., "Measurement of Nanoparticle Agglomerates by Combined Measurement of Electrical Mobility and Unipolar Charging Properties," *Aerosol Science and Technology*, 2010; 44:97-108.

\* cited by examiner

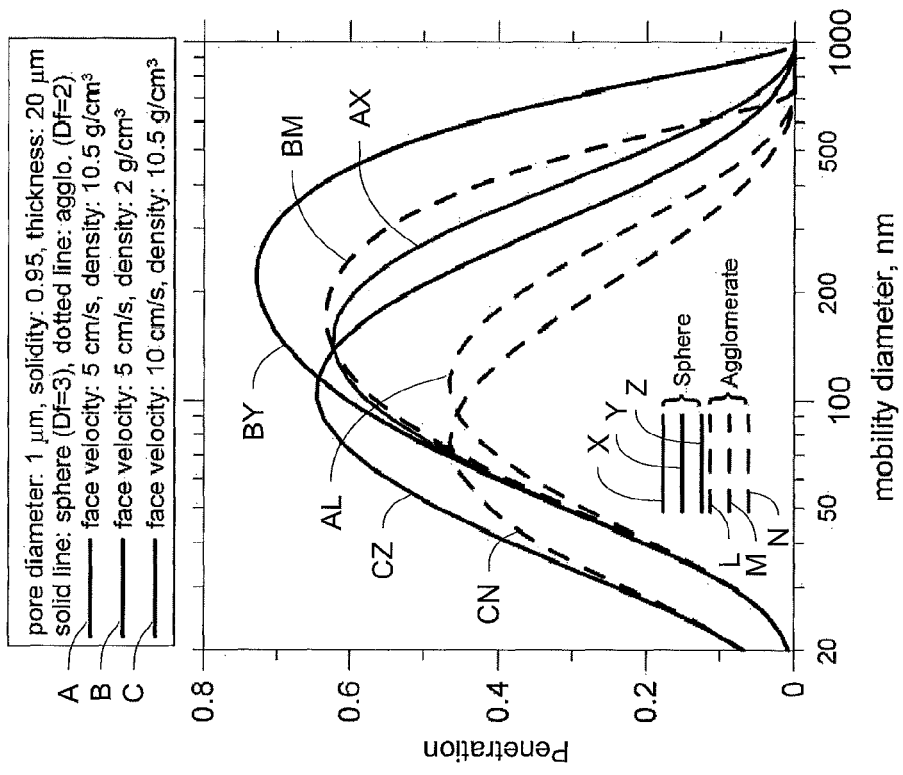
Fig. 4B  Model prediction—one microorifice plate, pore diameter=1 μm

Fig. 9    Capillary tube Model—Spurny et al. (1969, ES&T)

- The efficiency of impaction, $\varepsilon_I$ (Spurny et al., 1969):

$$\varepsilon_i = \frac{2\varepsilon_i'}{1+\xi} - \frac{\varepsilon_i'^2}{(1+\xi)^2} \quad (1)$$

where $\varepsilon_i' = 2\text{Stk}\sqrt{\xi} + 2\text{Stk}^2\,\xi\exp\left[\frac{-1}{\text{Stk}\sqrt{\xi}}\right] - 2\text{Stk}^2\xi$, $\xi = \frac{\sqrt{P}}{1-\sqrt{P}}$, $\text{Stk} = \frac{(2r)^2 C_c(2r)\rho_p q}{18\mu R_0}$ P: filter porosity, Stk: Stokes' number, r: particle radius, $C_c$: slip correction factor, $\rho_p$: particle density, q: face velocity, $\mu$: gas viscosity, $R_0$: pore radius

- The diffusion efficiency in tube wall, $\varepsilon_D$ (Spurny et al., 1969):

$$\varepsilon_D = 2.56 N_D^{2/3} - 1.2 N_D - 0.177 N_D^{4/3} \text{ for } N_D < 0.01$$

$$\varepsilon_D = 1 - 0.81904\exp(-3.6568 N_D) - 0.09752\exp(-22.3045 N_D) \\ - 0.03248\exp(-56.95 N_D) - 0.0157\exp(-107.6 N_D) \text{ for } N_D > 0.01 \quad (2)$$

where $N_D = \frac{LPD}{R_0^2 q}$, L: thickness of filter, D: particle diffusivity

- The interception efficiency on pore surface, $\varepsilon_R$ (Spurny et al., 1969):

$$\varepsilon_R = N_R(2 - N_R) \quad (3)$$

where $N_R = r/R_0$

Prior Art

*Fig. 10*

Capillary tube Model— Manton (1978; 1979, AE)

- The efficiency of impaction and interception, $\varepsilon_{IR}$ (Manton, 1978):

$$\varepsilon_{IR} = \{R_0(2 - R_0)\}^{2/(1+aR_0+2bR_0)} \quad (4)$$

where a and b are function of P, $R_0$: the ratio of particle radius to pore radius ($r_0$), P: filter porosity,

- The diffusion efficiency on filter surface, $\varepsilon_{DS}$ (Manton, 1979):

$$\varepsilon_{DS} = 1 - \exp\left\{-\alpha_1 \phi^{\frac{2}{3}} / \left[1 + (\alpha_1/\alpha_2)\phi^{7/15}\right]\right\} \quad (5)$$

where $\alpha_1 = 4.57 - 6.46P + 4.58P^2$, $\alpha_2 = 4.5$, $\phi = \frac{DP^{1/2}}{r_0 q}$, D: particle diffusivity, q: face velocity Prior Art

MEASUREMENT OF PARTICLE MORPHOLOGY USING FILTRATION

CROSS REFERENCE TO RELATED APPLICATIONS

This application is a continuation in part of International Application No. PCT/US2011/049340 filed 26 Aug. 2011, which was published in English on 1 Mar. 2012 as International Patent Publication No. WO 2012/027665 A1, and which claims the benefit of U.S. Provisional Application Ser. No. 61/377,550, filed 27 Aug. 2010, entitled "Measurement of Particle Morphology Using Filtration," which are all incorporated herein by reference in their entirety.

TECHNICAL FIELD

The present disclosure relates to the characterization of a totality of particles. For example, the particles may be aerosol particles, liquid-borne particles, and in particular microparticles and/or nanoparticles. Further, for example, the present disclosure can be applied in the fields of environmental analysis, protection at workplaces, or process monitoring.

BACKGROUND

"Aerosols" is the name used below to mean, in general, mixtures of solid and/or liquid suspended particles (also referred to in general as "particles" below) and gaseous media, for example, in particular air. Aerosols are meant to be, in particular, aerosols with particles in the micrometer range, that is to say in the range <1000 and/or, even preferably, in the nanometer range, that is to say in the range <1000 nm.

Examination and characterization of aerosols plays an important role in various areas of natural sciences, technology, medicine and daily life. By way of example, the surface characterization of aerosols and aerosol particles plays a critical role in the fields of environmental analysis and medicine, since the surface distribution and the surface morphology of aerosols can have a decisive influence on, for example, the toxicity of nanoparticles and, for example, the assessment of workplace pollution caused by aerosols and nanoparticles.

Knowledge of the structures of the particles, in particular of agglomerate structures, is indispensable for assessing workplace pollution of nanoparticles, parameterizing the inhalation-toxicological potential and process control in the synthesis of gaseous nanoscale particles. The on-line observation of particle formation is likewise of great interest in many other fields, for example, in meteorology and climate research or aerosol physics.

In particular, gas-borne nanoscale particles, i.e. particles having a size of, for example, <1000 nm, or else micrometer particles, i.e. particles having a size of, for example, <1000 µm, are often in the form of agglomerates or aggregates, i.e. sintered agglomerates, of so-called primary particles. The structures of the agglomerates are here, for example, loosely linked in the manner of a chain and/or branched, or may even be spherically sintered.

To characterize the particles or aerosols, a large number of different devices and methods have been developed which enable, on-line or off-line, important statements about characteristics of the particles to be made. As described herein, "off-line" measurements are measurements in which the measurement is effected independently of the flow, for example, with time displacement and/or in a separate apparatus. In contrast, "on-line" measurements are those which are carried out directly and without any major time displacement, for example, real-time measurements or measurements which are carried out at least nearly in real time.

The detection and counting of such particles already play an important role in characterization processes, in particular in the field of nanoparticles. A large number of different types of particle counters are known and available commercially and are based on different measurement principles. For example, one measurement principle is based on detection by way of light, for example, laser light. An example of such a laser particle counter is disclosed in WO 91/08459. Other particle counters or particle detectors for ultra small particles are based on charge effects, for example, a particle counter disclosed in WO 2007/000710 A2. Other on-line measurement techniques, such as those based on scattered light methods (for example, scattered laser light), are also known. Other counters and detectors are based on electrostatic principles, such as the particle sensor disclosed in WO 2007/000710 A2. It is also possible to use so-called condensation nucleus counters or condensation particle counters (CPC) in particular to be able to detect even very small particles, for example, particles in the lower nanometer range, which is comparatively difficult using conventional light techniques. In these counters or detectors, the size of the particles is artificially increased, for example, by way of depositing a film of condensate comprising, for example, butanol, such as by providing a condensate sleeve around these particles. The particles whose sizes are increased in this manner can then be detected comparatively easily. U.S. Pat. No. 4,790,650 discloses an example of a condensation particle counter.

Besides the pure detection and the counting of particles, classification, in conjunction with a corresponding detection of the particles, also plays a role. Conventionally, the particles are classified in an electrodynamic manner by categorizing the particles in accordance with their mobility, that is to say the ratio of the velocity of the particles to the force acting on the particles, into classes or fractions. In the case of electrically charged particles, in particular the so-called electrical mobility (often also referred to as Z) is used, i.e., the ratio of the velocity of the particles to the electric field acting on the particles.

The mobility of a body moving in a liquid or a fluid (gas or liquid) is usually expressed by the so-called mobility diameter $d_m$, which is frequently also referred to as mobility-equivalent diameter. This is the diameter of a fictitious sphere which has said mobility in the fluid (for example, the carrier gas used).

A large number of devices and methods have been developed for the classification, or, in other words, for separating the particles, for example, in accordance with their mobility. One example of such a device is the so-called differential mobility analyzer (DMA). These analyzers are generally variable electric filters which, for example, as a function of variable or fixedly pre-specified geometrical dimensions and/or of variable or fixedly pre-specified electric voltages, only allow particles of a specific electrical mobility from a particle flow to pass. Examples of such differential mobility analyzers are disclosed in WO 2007/1016711 A1. Classifiers of this type are frequently connected to corresponding counters which directly allow the number or concentration of particles in the specific, filtered-out class to be counted. It is possible in this manner, for example, to determine concentrations and particle size distributions of the totality of the particles by changing the class. Such instruments are referred to, for example, with minor structural differences, as "DMPS" instruments (differential mobility particle sizers), SMPS (scanning mobility particle sizers) or FMPS (fast mobility particle sizers). Examples of such classifier systems, which are connected directly to measuring instruments or counters, are disclosed, for example, in U.S. Patent Publication No. 2006/0284077 A1, in U.S. Patent Publication No. 2004/0080321 A1, in GB 2378510 A, in GB 2374671 A, in GB 2346700 A, or in WO 99/41585.

Since charging particles or particle flows plays an important role in many methods or devices known in the art, a large number of devices have been developed which can produce defined charges on the particles. These devices, also referred to below as "charge state generators" or "chargers," can produce, for example, specific charge distributions (for example, probabilities that a particle accepts one, two or more positive and/or negative elemental charges) or a fixedly pre-specified number of such charges on the particles. An example of such devices is disclosed in EP 1 678 802 A2, in WO 00/78447 A1 (there in connection with a DMA and a CPC), or in DE 198 46 656 A1. If the same number of positive and negative charges are produced, such charge state generators are frequently also referred to as neutralizers, such as is disclosed, for example, in U.S. Pat. No. 6,145,391.

As described above, in the on-line characterization of particles, in particular aerosols, spherical equivalent particle sizes are generally assumed. This is, for example, a foundation of the above-mentioned DMPS, SMPS and FMPS methods, since the mobility diameter $d_m$ is always used. However, this could potentially result in significant errors if the ascertained characteristic values are further used. By way of example, different types of agglomerates cannot be differentiated. In addition, the error in the diameter also comes into play in the volume calculation of the particles to the power of three and thus also, for example, the mass calculation of the particles (if the density is known). The resulting errors in the determination of the mass concentration are significant. The inaccuracies of the known methods and devices also become very noticeable in the calculation of the particle surface areas, in which the errors in the diameter come into play to the power of two. This is a significant disadvantage of the known methods and devices, in particular in the field of toxicology, where the surface areas and surface distributions of the particles play a significant role. In addition, shape factors, in which, for example, the differences between rod shape, spherical shape, plate shape or similar shape differences come into play, can hardly be detected using the known methods.

Therefore, the on-line determination of the primary particle diameter, of the number of primary particles per agglomerate particle and of the shape factors of the agglomerates and other structure-specific parameters can overall hardly be carried out using the commercially available measurement methods. In order to determine those parameters, off-line measuring methods are conventionally used, in which some of the particles are taken from the totality, for example, by way of samplers, in order to introduce them into other characterization methods. By way of example, these other characterization methods can be imaging characterization methods, for example, scanning electron microscopy (SEM), transmission electron microscopy (TEM), or atomic force microscopy (AFM). Examples of samplers of this type, with which samples can be taken from the totality, are disclosed, for example, in WO 2004/009243 A1 or in JP 2007127427 A. The off-line methods described are, however, expensive and time consuming, and, in particular, do not permit on-line characterization and/or control, based on the evaluation of the characterizations, for example, of process parameters, manufacturing parameters, or safety measures in the field of protection at workplaces.

Further approaches for solving the above-mentioned problems of the particle diameters are based on the fact that the particle diameters are determined, rather than a metrology method, on the basis of charging theories and theories relating to drag forces acting on agglomerates. An example of such a theoretical or semi-empirical method can be found in "On-line measurement of ultrafine aggregate surface area and volume distributions by electrical mobility analysis: I. Theoretical analysis," Aerosol Science 37 (2006) 260-271 by A. A. Lall et al. and in "On-line measurement of ultrafine aggregate surface area and volume distributions by electrical mobility analysis: II. Comparison of measurements and theory," Aerosol Science 37 (2006) 272-282 by A. A. Lall et al. The model described therein combines a mobility analysis, carried out by means of a DMA or an SMPS, with calculations relating to the drag force acting on agglomerates and the charging efficiency of agglomerates. A theoretical approach is used which is based on a large number of assumptions which are restrictions at the same time. For example, it is assumed that the agglomerates comprise primary particles. The latter must be spherical and have a primary particle size which is already known in advance. Furthermore, the surface of the agglomerates must be accessible. This means that primary particles do not cover each other which, for example, rules out aggregates having primary particles which are clearly fused together. Such a method can therefore not be applied to partially sintered agglomerates (aggregates). Overall, the described model therefore comprises a large number of model-based restrictions and assumptions which must be met so that the model provides realistic results.

SUMMARY

An exemplary system for characterizing a totality of particles may include a classification apparatus to select a class of the totality of particles having a defined mobility, a first particle counter apparatus positioned in a first path of the system for use in determining total particle concentration of a class of particles; and a filter apparatus positioned in a second path of the system (e.g., the filter apparatus may be defined such that particles of a class with different morphologies correspond to different penetration levels therethrough). The system may further include a second particle counter apparatus positioned in the second path for use in determining a filtered particle concentration indicative of particles of a class which penetrate the filter apparatus and a calibrator apparatus configured to determine at least one morphological parameter based on the fraction of particles of a class penetrating the filter apparatus (e.g., the fraction may be determined as a function of the total particle concentration and the filtered particle concentration, and further, the at least one morphological parameter may include at least information about the particles of the class penetrating the filter apparatus).

One or more embodiments of the system may include one or more of the following features: the calibrator apparatus may be configured to determine at least one morphological parameter based on a fractional penetration level defined as the ratio of the filtered particle concentration to the total particle concentration; the at least one morphological parameter may include particle maximum length and/or fractal dimension; the calibrator apparatus may include a controller apparatus (e.g., wherein the controller apparatus may include at least one processing apparatus for executing instructions of one or more programs to determine at least one morphological parameter based on the fraction of particles of a class penetrating the filter apparatus and correlation information); the correlation information may include at least information correlating different morphologies of particles to different levels of penetration through a defined filter apparatus; the correlation information may include at least information correlating different morphologies of particles to different levels of penetration through a defined filter apparatus at one or more different face velocities; the system may include a line system for guiding a flow of particles (e.g., wherein the classification apparatus, the first particle counter apparatus, the filter apparatus, and the second particle counter apparatus may be connected in the line system); the system may further include a charge apparatus for charging the totality of particles (e.g., the charge apparatus may be located upstream of the classification apparatus in the line system); each of the first and second particle counter apparatus may include an electrometer; each of the first and second particle counter apparatus may include a condensation particle counter; and the filter apparatus may include at least one of a screen filter, a fibrous filter, a membrane filter, and a multi-micro-pore filter (e.g., a multi-micro-pore filter having a pore diameter in the range of 0.005 μm to 100 μm).

An exemplary method for characterizing a totality of particles may include selecting a class of the totality of particles having a defined mobility; determining the total particle concentration of the class of particles; providing a filter apparatus (e.g., wherein the filter apparatus may be defined such that particles in the class with different morphologies have corresponding different penetration levels therethrough); filtering the class of particles using the filter apparatus and determining a filtered particle concentration indicative of the particles of the class which penetrate the filter apparatus; and determining at least one morphological parameter based on the fraction of particles of a class penetrating the filter apparatus (e.g., the fraction may be determined as a function of the total particle concentration and the filtered particle concentration, and further the at least one morphological parameter may include at least information about the particles of the class penetrating the filter apparatus).

In one or more embodiments of the method, one or more of the following features or processes may be included: determining at least one morphological parameter based on the fraction of particles of a class penetrating the filter apparatus may include determining a fractional penetration level defined as the ratio of the filtered particle concentration to the total particle concentration and determining the at least one morphological parameter based on the fractional penetration level; the at least one morphological parameter may include maximum particle length and/or fractal dimension; determining the at least one morphological parameter may include determining the at least one morphological parameter based on the fraction of particles of a class penetrating the filter apparatus and correlation information (e.g., the correlation information may include at least information correlating different morphologies of particles to different levels of penetration through a defined filter apparatus, the correlation information may include at least information correlating different morphologies of particles to different levels of penetration through a defined filter apparatus at one or more different face velocities, etc.); the method may further include charging the totality of particles prior to selecting the class of particles; determining the total particle concentration of the class of particles and determining a filtered particle concentration of the class may include using an electrometer and/or using a condensation particle counter; the filter apparatus may include at least one of a screen filter, a fibrous filter, and a membrane filter.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWING

FIG. 4B shows an illustration of the penetration differences of different particles through a defined filter (e.g., a micro-pore filter) at different face velocities.

FIG. 9 is an illustration of a Spurny particle penetration model.

FIG. 10 is an illustration of a Manton particle penetration model.

DETAILED DESCRIPTION OF EXEMPLARY EMBODIMENTS

Figure 1:
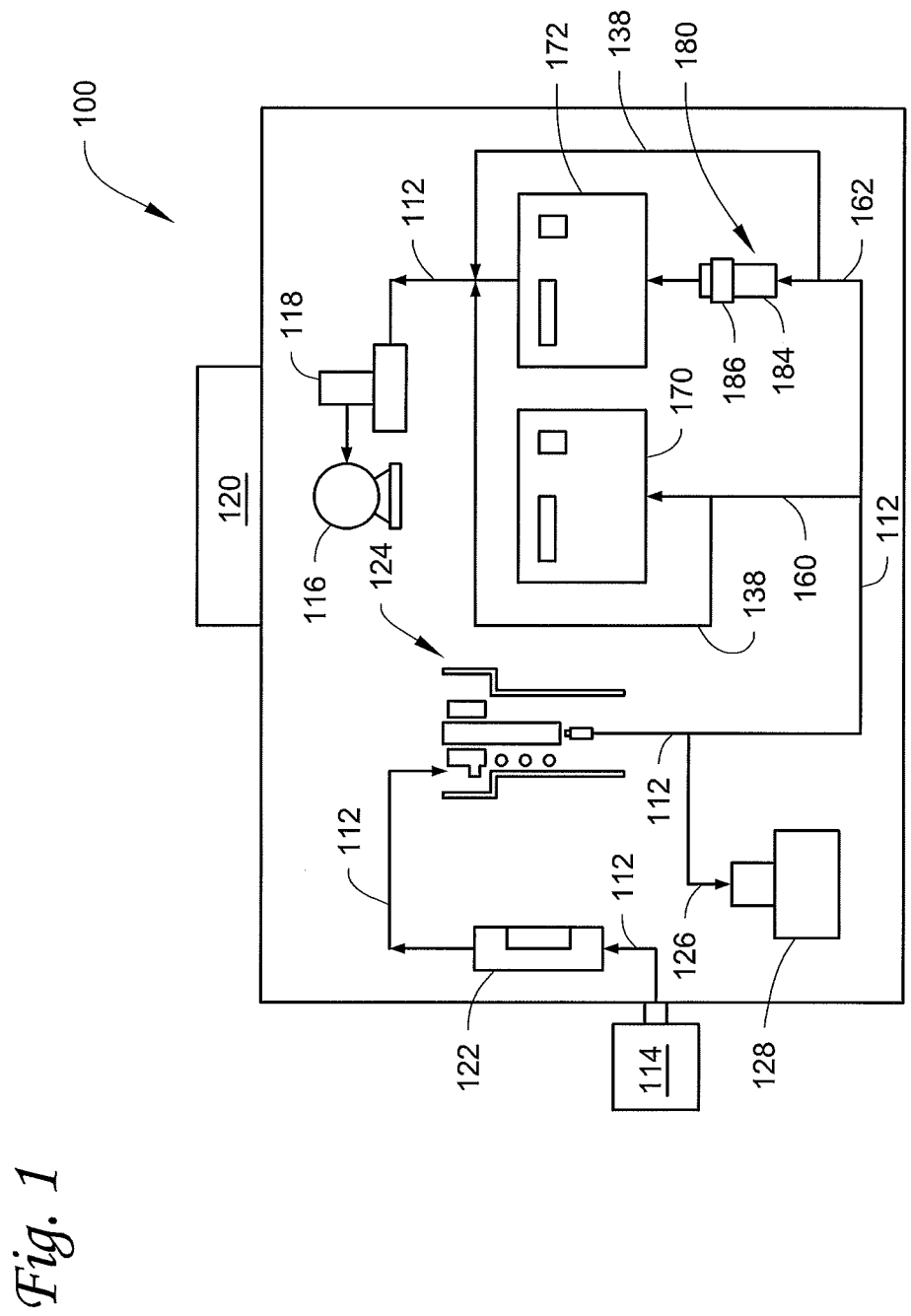
FIG. 1 shows an exemplary embodiment of a measurement system according to the present disclosure.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural/process changes may be made without departing from the scope of the present disclosure. Unless stated otherwise herein, the figures of the drawing are rendered primarily for clarity and thus may not be drawn to scale.

Methods herein are described in a particular illustrated order. However, orders other than the one illustrated are feasible. It is furthermore feasible that additional process steps not listed in the method may be carried out. It is additionally possible for individual method steps or groups of method steps to be carried out repeatedly or to be carried out such that they overlap at least partially in terms of time.

WO 2009/098215 A1, entitled "Measurement System for the MultiDimensional Aerosol Characterization" addresses one or more of the problems describe above. As described therein, for example, methods and devices for characterizing a totality of particles are described. For example, the methods and the devices described therein are capable of determining at least one morphological parameter from the charge Q, the number N, and the mobility $d_m$ of a class of particles selected from its totality.

For example, the method described in WO 2009/098215 A1 includes a classification step. In the classification step, a class of the totality is selected, wherein the particles of the selected class have a pre-specified mobility $d_m$. "Mobility" is to be regarded in broad terms and depends on the method used for the classification. In general, the term is meant to describe a connection between a movement state assumed by a particle as a reaction to an action of a force and the force itself. An example of this is proportionality constant. The exact definition of the mobility can in particular depend strongly on the classification method used. An example of this is electrical mobility. In diffusion separators, it may be, for example, a diffusion equivalent diameter, in nano-impactors it may be an impaction equivalent diameter, and in mass analyzers it may be a mass equivalent diameter. It may in particular also be a mechanical mobility or, an electrodynamic mobility. Alternatively, or in addition, to a specific mobility in the actual sense, however, it is also possible to use a variable which is uniquely related to the mobility. Therefore, the description herein will express the term "mobility" using the mobility diameter, likewise denoted by the term $d_m$, without restricting further possible definitions. As illustrated above, an assumption in the case of this mobility diameter is that the particle is a sphere with the mobility diameter, $d_m$.

When selecting the class, a fixedly pre-specified mobility can be selected. Alternatively, or additionally, which will generally be the case in practice, however, the pre-specified mobility will include an open, half-open or closed interval of mobilities since even the most exact classification method always has a certain minimum resolution or since a mobility interval is intended to be selected deliberately.

In order to carry out the classification step, it is possible to use, as explained in more detail in the description of the device below, in principle all known classification methods and/or classification devices, for example, the classification methods known from the prior art, which were described in the Background herein. For example, electrostatic classification methods, such as using a DMA, may be used.

"Selecting" is herein understood as meaning that the selected class of remaining particles is separated from the totality in order to use this selected class separately. By way of example, the totality of the particles may be present in a storage container and/or a line system, where the selected class is output, for example, into a selection container and/or a line system.

The method described in WO 2009/098215 A1 also includes a counting step. In this counting step, a number N of the particles of the selected class is determined. A "number" can in turn be understood to mean directly a number of a limited quantity of the selected class. This may be the case in particular if the particles of the selected class are made available, for example, in a closed vessel or if the selected class is closed in another manner. Alternatively, or additionally, to the determination of the absolute number of particles of the selected class, however, it is also possible in turn for a variable correlating directly to the number to be used, for example, a particle flow rate. This is especially expedient if the selected class is continuously made available, for example, in the form of a particle flow of the selected class being made available continuously. In this case a particle flow rate, that is to say, for example, a number of particles flowing through a flow pipe per time unit, a volumetric flow rate or the like can be stated as number N.

In order to carry out the counting step, it is possible in principle for all known counting methods to be used, for example, the above-described counting methods known from the prior art. For possible embodiments, reference in turn made to the following description of the device or to the exemplary embodiments in WO 2009/098215 A1.

The method described in WO 2009/098215 A1 further includes a charge determination step, wherein the charge Q of the particles of the selected class is determined. Analogously to the number N of the particles, it is possible in turn to determine an absolute charge, for example, an absolute charge of a closed quantity of the selected class of the particles and/or an absolute quantity of particles present in a pipe section of a line system or in a measurement chamber. The total charge or, if the number of the particles is known, an average charge can be determined here. Alternatively or in addition to a total charge, it is also possible in turn to use, analogously to the number N of the particles, correlating variables, for example, the electric current I or the electric current density. For example, the charge flowing per time unit, i.e., the electric current I, can be determined. This is expedient in particular in the above-described case where measurements are carried out continuously, e.g., where the selected class is made available continuously. It is possible in principle for all methods for charge determination known from the prior art to be used. For example, a current I measured using an NSAM can be used directly as "charge Q".

Still further, the method described in WO 2009/098215 A1 includes an evaluation step, wherein the at least one morphological parameter is determined from the charge Q, the number N and the mobility $d_m$. As described therein, the morphological parameter includes morphological information about an agglomerate state of the particles. This morphological parameter can include, for example, one or more numbers, vectors, matrices, or, further, for example, classifications into morphological classes. In at least one embodiment, the at least one morphological parameter includes at least one of the following items of information: information about a categorization into morphological agglomeration classes, in particular a distinction between loose agglomerates, partially aggregated particles and aggregates; a number of primary particles per particle; a primary particle size "a"; a primary particle size distribution; and a shape factor.

A primary particle size "a" herein means the size (for example, the diameter and/or the radius) of primary particles from which the individual particle is made up. Such primary particles can generally be determined in conventional methods, for example, by way of off-line measurements, for example, imaging off-line measurements, since in particular agglomerates are generally made up of, for example, round primary particles or other types of primary particles of simple geometry which can be determined easily (for example, by way of image evaluation methods, for example, by means of matching circles and/or other geometric base elements, such as squares and rectangles, to a two-dimensional image). In particular in the case of agglomerates, it can be assumed in a first approximation that the sum of the surface areas of the primary particles forms the surface area of the total particle and/or that the sum of the volumes of the primary particles forms the volume of the total particle. It is also analogously possible, for example, to estimate primary particle size distributions, for example, by taking into account average primary particle sizes or primary particle size distributions within a particle.

As explained in WO 2009/098215 A1, it is possible to establish an at least largely unique relationship between the variables Q, N and $d_m$ and the morphological parameter. This relationship can be obtained, for example, with the use of empirical, semi-empirical or analytical or theoretical considerations. By way of example, this relationship can be recorded in the form of a single-variable function, a multi-variable function, a graph, a value table, an electronic table or in similar form and used in the evaluation step.

As set forth in WO 2009/098215 A1, the method described therein enables an on-line characterization of the particle totality since, on the basis of the morphological parameter which can be determined on-line, a large number of further characteristic variables (referred to below as "target variables") can be determined, such as surface area, volume, primary particle number per agglomerate or aggregate, internal porosity and/or an agglomerate or aggregate porosity, apparent density, agglomerate or aggregate density or the like. It is thus possible to determine a large number of further structure parameters, in particular of nanoscale agglomerates, from the measurement variables, which can preferably be done without the aid of off-line analysis. As WO 2009/098215 A1 provides a change from the simple sphere model of the mobility diameters towards a more realistic model which takes morphological aspects into account, for example, a primary particle model, it is possible to determine the target variables with a significantly higher degree of accuracy than is possible in known methods and devices. In this manner, in particular toxicities, environmental compatibility, reactivities or similar properties of the particles can be predicted or estimated much better than is the case with conventional methods. Since the measurement can be carried out on-line, the method can, in addition, be implemented without problems in a quick and cost-effective manner in various available measurement apparatuses, for example, for open-loop and/or closed-loop process control.

The proposed method of WO 2009/098215 A1 in its basic form illustrated above, and further as described in WO 2009/098215 A1, can be developed further advantageously in a variety of ways as described therein. For example, the methods illustrated in WO 2009/098215 A1 describe the determination of the morphological parameter for the respectively selected class. However, as already explained, the method steps can also be repeated. This is useful in particular for a so-called scan, that is to say a method in which different classes with different mobilities $d_m$, i.e., mobilities which at least do not coincide completely, are selected one after the other. For these different classes, the morphological parameters are then determined in each case according to the described method, with the result that a primary particle size distribution as a function of the mobility $d_m$ can be ascertained. To this end, it is possible to carry out the various steps, such as the classification step, the counting step, and the charge determination step, of the method repeatedly. The evaluation step can likewise be repeated or all the variables ascertained in the prior steps can, in a subsequent overall evaluation step, be evaluated and converted to a distribution of the morphological parameter, for example, a primary particle size distribution as a function of the mobility $d_m$. As already indicated herein, it is possible to infer from this distribution a large number of other distributions, for example, a surface distribution, a primary particle size distribution, a volume distribution, a mass distribution, a shape factor distribution or similar distributions.

As described herein, the morphological parameter includes morphological information about an agglomerate state of the particles. This morphological parameter can include, for example, one or more numbers, vectors, matrices or else classifications into morphological classes. In at least one embodiment, the at least one morphological parameter comprises at least one of the following items of information: information about a categorization into morphological agglomeration classes, in particular a distinction between loose agglomerates, partially aggregated particles and aggregates; a number of primary particles; a primary particle size "a"; a primary particle size distribution; and a shape factor.

The devices, systems, and methods described herein which use a filtration apparatus to characterize particles, as well as one or more steps or components described below with respect thereto, may be used alone and/or in combination with those described in WO 2009/098215 A1 to characterize a totality of particles. For example, the methods described in WO 2009/098215 A1 may not be suitable to provide the entire desired morphology of a class of particles. For example, agglomerate/aggregate particles usually have complicated structures and morphologies which need to be characterized by multiple structural parameters, such as, for example, the mobility diameter $d_m$, the primary particle diameter "a", the fractal dimension $D_f$, the maximum length, the aspect ratio, etc. The systems and methods described in WO 2009/098215 A1 enable, for example, measurement of $d_m$ and "a", but may not, in certain cases, be able to effectively determine other structural parameters, such as, for example, fractal dimension. To determine more structural parameters, other measurements, independent from (and/or in combination with) the method described in WO 2009/098215 A1, can and may need to be used. For example, as described herein, systems and methods may use filtration to obtain one or more other measurements related to the particle structure and morphology. The methods and systems may be independent from the electrical charging method described in WO 2009/098215 A1, and, for example, allow for determination of at least another structural parameter, for example, the fractal dimension $D_f$.

As previously discussed in the Background herein, nanoparticles form one of the founding blocks of the emerging nanotechnology. The amount of manufactured nanoparticles will grow significantly in the coming years. Nanoparticles are also pervasive in atmospheric sciences and air pollution. Morphologies of nanoparticles include compact spheres, agglomerates with compact or open structures, nanowires or nanotubes. The morphology of nanoparticles plays an important role in determination of the properties and functionalities of the nanoparticles.

Figure 3:
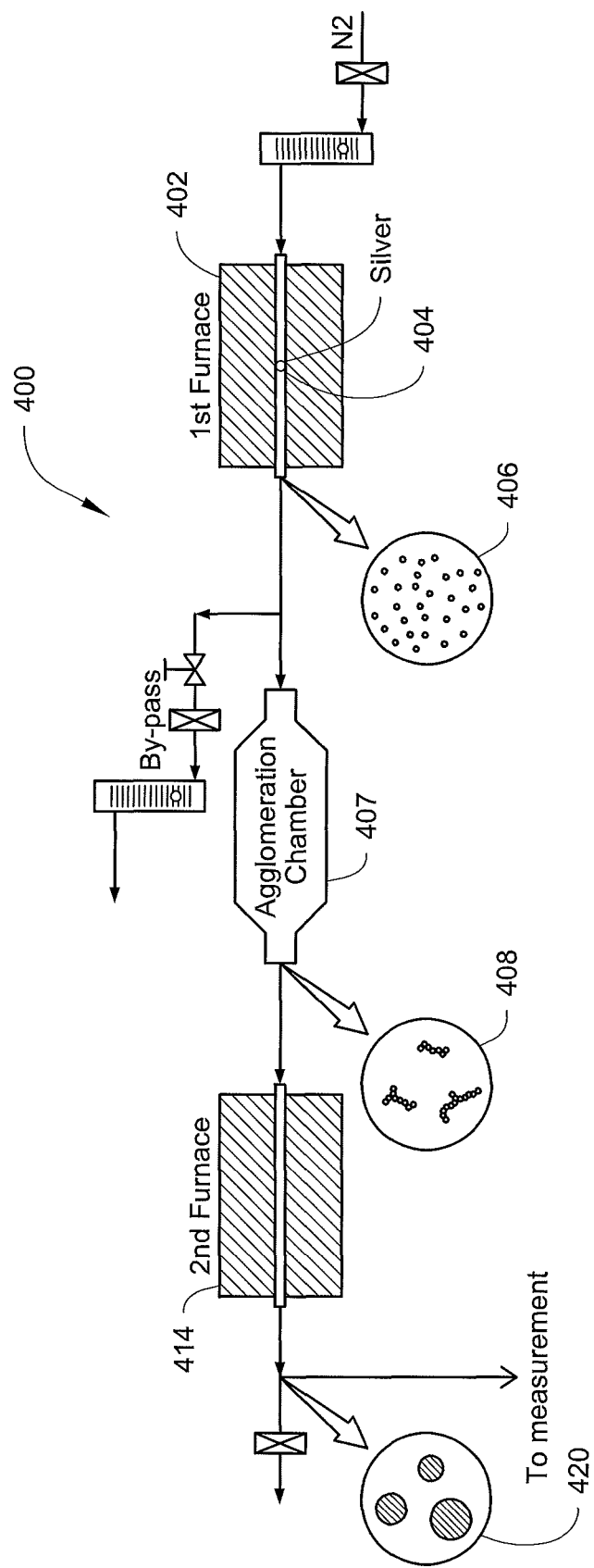
FIG. 3 is a schematic representation of an exemplary generation system for generating silver nanoparticles with different morphologies, which can be used to test the systems and methods described herein (e.g., such as shown in FIGS. 1 and 2).

Such nanoparticles may be generated in many different manners. FIG. 3 shows one exemplary method that includes use of a tandem-furnace system 400 which can generate silver nanoparticles of different morphologies (e.g., which nanoparticles can be used for the purpose of testing the methods and systems described herein). The system 400 includes a first electric furnace 402 used to generate silver nanoparticles from a pure silver powder source 404, which is vaporized and condensed into silver nanoparticles 406. These primary particles 406 stick upon collision to form nanoparticle agglomerates 408 in an agglomeration chamber 407 located just downstream of the first electric furnace 402. Agglomerate sintering is carried out in a second furnace 414 of the system 400 with various temperatures from room temperature to 600° C. Open-structured agglomerates are obtained at the room temperature. As the sintering temperature increases, the particle structure becomes more compact and the fractal dimension becomes larger. Spherical silver particles 420 are achieved at 600° C. sintering temperature.

Measurement of the morphology of airborne nanoparticles (e.g., such as those generated using the system 400 shown in FIG. 3) is not an easy task. One of the most common methods is electron microscopy. However, sample preparation, taking electrical micrographs and performing image analysis can be time consuming and expensive. Fast and on-line measurement for aerosols is required in many scenarios including measuring fast changing aerosols, quality control for material manufacturing, monitoring toxic airborne nanoparticles, etc. Most of the current aerosol instruments are designed for spherical particles. Therefore, there is a need for instruments and processes capable of fast and on-line measurement of morphology of nanoparticles, e.g., airborne nanoparticles, even in addition to those described in WO 2009/098215 A1.

As described herein, at least one embodiment of the present disclosure uses a filtration system to measure airborne nanoparticle morphology. Various filtration systems used in studying filtration efficiency, for example, are described in Kim, et al., "Structural Property Effect of Nanoparticle Agglomerates on Particle Penetration through Fibrous Filter," *Aerosol Sci. & Technology*, 43, 344-355 (2009) and Lange, et al., "Predicting the Collection Efficiency of Agglomerates in Fibrous Filter," *Particle & Particle Systems Characterization* 16:60-65 (1999).

Figure 4A:
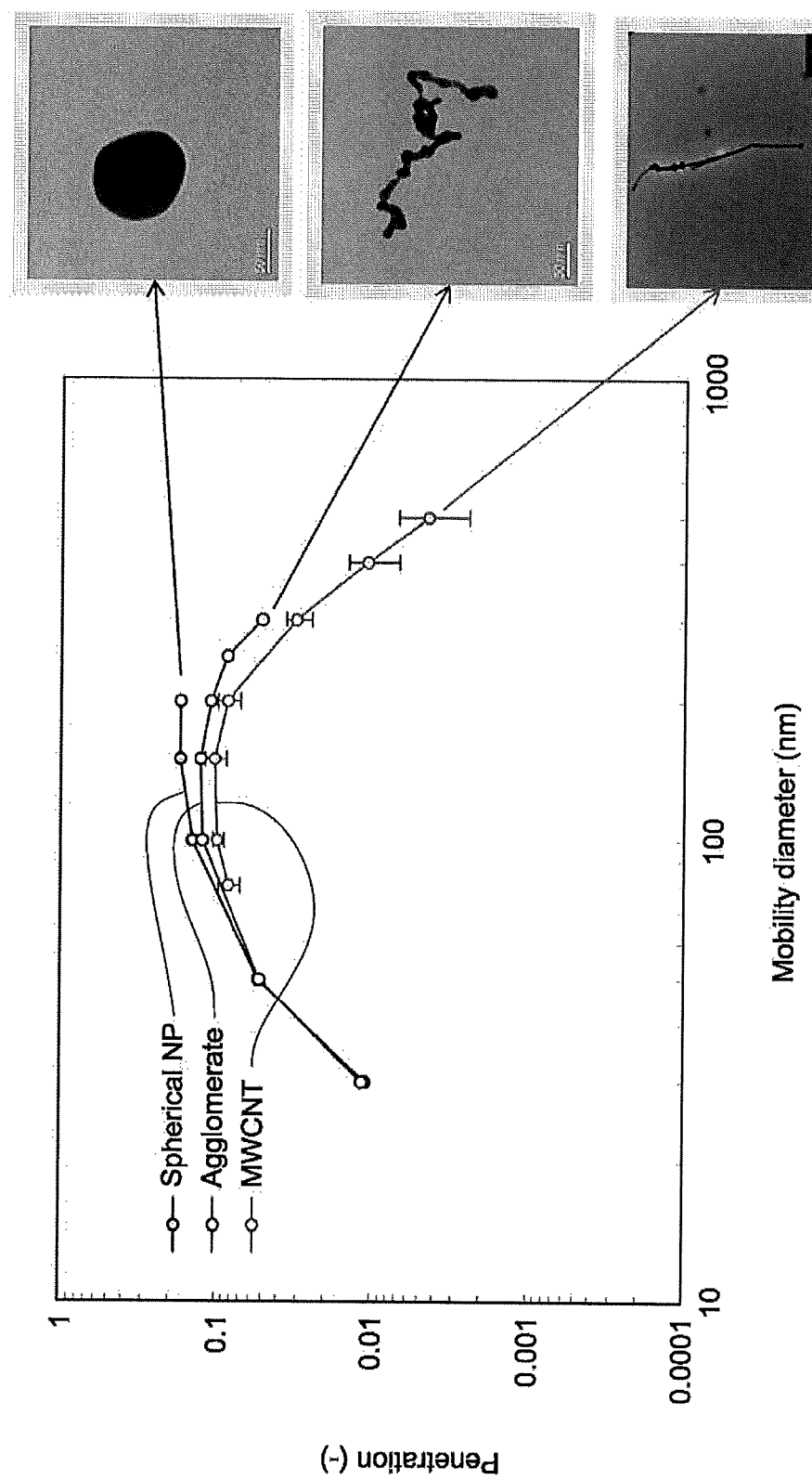
FIG. 4A shows an illustration of the penetration differences of different particles through a defined filter (e.g., a fibrous filter).

FIG. 4A herein shows experimental results for penetration of spherical nanoparticles (NP), silver nanoparticles agglomerates, and multi-wall carbon nanotubes (MWCNTs) through a fibrous filter. Such experimental results shown in FIG. 4A indicate that when the mobility size of such particles is above 100 nm, the penetration of loose agglomerates through a filter is considerably lower than that of spherical particles, and the penetration of carbon nanotubes is even lower. The interception mechanism plays an important role for particles in the range of 100 nm and above. It is believed that, for example, the carbon nanotubes and agglomerates have open structures and extended branches and are more probable to be intercepted by the filter fibers, which leads to lower penetration. Thus, it has been determined that the different penetration values through a defined filter can be correlated to the morphology of the particles. For particles less than 100 nm, the physical behaviors of spheres and agglomerates may be similar.

FIG. 4B herein shows predicted model results (e.g., using the Manton-Shapiro model as further described herein) for penetration of spherical particles (X,Y,Z) and agglomerate particles (L,M,N) through a micro-orifice plate filter (e.g., a filter as defined in FIG. 4B). Such predicted model results shown in FIG. 4B indicate that varying the face velocity of the same particles being provided to a defined filter (e.g., the velocity thereof as they approach the filter face of the defined filter) results in variation of the penetration of particles through the filter; which provides varied penetration curves (e.g., filtration efficiency curves) for such varied face velocities. Thus, the different penetration values through a defined filter can be correlated to the morphology of the particles based at least in part on the penetration at the one or more face velocities. For example, as shown in FIG. 4B, the penetration differences between spheres and agglomerates indicative of particle morphology may extend to smaller size particles by increasing face velocity used in a measurement system for determining particle morphology, the penetration differences between different agglomerates may be indicative of particle morphology of such agglomerates (e.g., different maximum lengths and/or fractal dimensions) based on the penetration of particles through a defined filter at different face velocities, etc. Further, for example, if the filtration results at several different face velocities are combined together, more than one particle parameter may be obtained from the combined results. For example, as shown in FIG. 4B, morphological parameters indicative of whether the particle is a sphere or an agglomerate (e.g., the maximum length, fractal dimension, etc.) and the particle density may be determined by using the filtration results at several different face velocities.

Generally, as described herein in at least one embodiment, a measurement system that includes a filtration system is used for determining one or more morphological parameters of particles being characterized. Such use of a filtration system may include providing a totality of particles (e.g., airborne or liquid-borne nanoparticles) to be first size selected by a classification apparatus, such as a differential mobility analyzer (DMA). Then, for example, the selected particles with the same electrical mobility diameter, which have electrical charges on them, may be sent to, for example, two parallel paths. The total particle concentration is measured by a particle detection apparatus, such as a counter (e.g., a first electrometer) in the first path. A classifying filter apparatus is installed in the second path which leads to different penetration values dependent on the particle morphology of the selected particles. The concentration of the particles penetrating through the classifying filter apparatus will be measured by a particle detection apparatus, such as a counter (e.g., a second electrometer). At least in one embodiment, thereafter, the ratio of the measurements of the two electrometers is representative of the fractional penetration. The system can be calibrated using particles with similar morphology and different morphologies (e.g., spherical, loose agglomerate, and fiber-like structures can be applied in the calibration). Then, for example, the value of the fractional penetration can be correlated to one or more particle morphology parameters, such as the fractal dimension.

Although one or more different particle detection apparatus may be used as described further herein, the use of one or more specific detection apparatus may be beneficial over others. For example, the use of electrometers, may allow for faster particle detection and may be able to give a time resolution of one second or less. Such may not be true with the use of condensation particle counters. The filtration system can lead to real time measurement of nanoparticle morphology.

A method 300 for characterizing a totality of particles is described with reference to FIG. 2. Such a method 300 may be implemented, for example, with the system 100 shown in FIG. 1, or any other system suitable for carrying out the functionality of the process to determine one or more morphological parameters, such as, for example, fractal dimension. Like the one or more methods described in WO 2009/098215 A1, method 300 provides a process in which no assumptions or known information about the particle morphologies need to be used, but, for example, where a distinction can be made in a metrological manner between whether loosely sintered agglomerates, partially sintered aggregates or completely sintered, i.e., for example, nearly spherical, agglomerates are present.

The method 300 includes providing a totality of particles (e.g., as an input to a measurement system) (block 304). For example, a totality herein may be a quantity of particles, such as solid particles and/or droplets as suspended particles, wherein the quantity includes a large number of the particles, such as more than 100 particles, and, for example, more than 1000 particles, or a flow of particles. This totality of particles may be an aerosol, that is to say a totality of gas-borne particles, for example, particles in air. The particles may be microparticles and/or nanoparticles. Further, for example, the system including the filtration apparatus described herein can be applied to liquid-borne particles as well, such as, for example, colloidal suspensions.

The method 300 provides for characterization of particles, such that at least one item of morphological information can be obtained in the process directly or at least indirectly, e.g., maximum length and/or fractal dimension. The morphological information, referred to herein as a "morphological parameter," is intended to comprise an item of morphological information about an agglomerate state of the particles, and to be more precise information about whether the particles are present in the form of loosely sintered (such as chain-type or branched) agglomerates, as partially sintered aggregates, or as completely sintered aggregates, or agglomerates. For example, identification of the particles as nanotubes may be accomplished. Nanotubes typically refer to particles with a one-dimensional structure with an aspect ratio much larger than one. The fractal dimension of nanotubes is usually considered to be one, similar to a chain agglomerate with no branches. The nanotubes can be described by their length and diameter, similar to the maximum length and primary particle diameter of a chain agglomerate without branches.

Accordingly, a categorization into morphological classes, for example, may be carried out. However, alternatively, or in addition, to an item of information about a categorization into morphological agglomeration classes, the at least one morphological parameter can comprise further information, e.g., maximum length, fractal dimension, a shape factor (that is a factor which differentiates, for example, between plate shape, rod shape, tube shape or similar morphologies), etc.

In furtherance of the process to characterize the totality of particles, the method 300 includes selecting a class of the totality of particles having a defined mobility (block 308) (e.g., a classification of the totality of particles). In a manner similar to that described in WO 2009/098215 A1, a class of the totality is selected, wherein the particles of the selected class have a pre-specified mobility $d_m$. "Mobility" is to be regarded in broad terms and depends on the method used for the classification. In general, the term is meant to describe a connection between a movement state assumed by a particle as a reaction to an action of a force and the force itself. An example of this is a proportionality constant. The exact definition of the mobility can in particular depend strongly on the classification method used. An example of this is electrical mobility. In diffusion separators, it may be, for example, a diffusion equivalent diameter, in nano-impactors it may be an impaction equivalent diameter. It may in particular also be a mechanical mobility or, an electrodynamic mobility. Alternatively, or in addition, to a specific mobility in the actual sense, however, it is also possible to use a variable which is uniquely related to the mobility. Therefore, the description herein will express the term "mobility" using the mobility diameter, likewise denoted by the term $d_m$, without restricting further possible definitions. As illustrated above, an assumption in the case of this mobility diameter is that the particle is a sphere with the mobility diameter, $d_m$.

When selecting the class, a fixedly pre-specified mobility can be selected. Alternatively, or additionally, which will generally be the case in practice, however, the pre-specified mobility will include an open, half-open or closed interval of mobilities since even the most exact classification process always has a certain minimum resolution or since a mobility interval is intended to be selected deliberately.

In order to carry out the class selection, it is possible to use, as explained in more detail in the description herein, in principle all known classification methods and/or classification devices, for example, such as the classification methods known from the prior art, which were described in the Background herein. For example, electrostatic classification methods, such as performed by a DMA, may be used.

"Selecting" is herein understood as meaning that the selected class of remaining particles is separated from the totality in order to use this selected class separately. By way of example, the totality of the particles may be present in a storage container and/or in a line system, where the selected class is output, for example, into a selection container and/or into a line system.

Charging of the totality of particles prior to selection may also be carried out. For example, it is possible for a defined charge state of the particles and/or of the selected classes to be established. A defined charge state is here understood to refer to a state in which either the charge of each particle of the particles and/or of the selected class is known or in which a charge distribution of the particles or of the class of the particles is known. The charge state can be achieved by virtue of the fact that the particles have overall a total charge which is different from zero, or it is possible, depending on expediency, for an overall neutrality to be established, such that the positive and negative charges cancel each other out overall. The latter case is often also referred to, somewhat confusingly, as "neutralization", since neutrality prevails overall, although charged particles are still present.

Generally, the charging of the particles may be carried out before the selection of the class from the totality of particles. To carry out the charge process, it is possible in principle to use all methods known in art to establish a defined charge state, for example, using the methods and devices known in art, in particular so-called chargers. Thus, e.g., the charging of the particles may include the use of ionized particles or ionized particle beams and/or the use of ionizing radiation, such as ionizing particle rays and/or ionizing electromagnetic radiation. For example, charging of the particles may include the use of radioactive radiation and/or electromagnetic radiation.

The charge generation may be performed in a direct or indirect way. Thus, the charge may be generated in and/or transferred to the particles directly, such as by directly ionizing the particles. Alternatively or additionally, an indirect way of charging may be used. Thus, the charges may be generated in or on separate carriers, such as on carrier gas molecules, e.g. on air molecules, and, subsequently, transferred from the charged carriers onto the particles, such as by diffusion of the charged carriers towards the particles. The latter principle is generally known as "diffusion charging." Diffusion charging (e.g., such as with a bipolar diffusion charger) provides the advantage of the charging being widely independent from the material of the particles. Making use of diffusion charging, silver particles, for example, generally may be charged the same way as polymer particles or particles made of other types of insulating materials. Typically, besides the carrier (such as a carrier gas), diffusion chargers include one or more radioactive materials, preferably materials emitting rays such as alpha-rays and/or beta-rays which are able to ionize gas molecules.

The selected class of particles (e.g., selected based on a defined mobility) is then provided down two paths 310, 312 for operation thereon. For example, in path 310, the total particle concentration of the class of particles directed down the path 310 is determined (block 320).

Like the method described in WO 2009/098215 A1, such a total concentration determination may be performed with use of a particle detector apparatus (or, sometimes referred to herein as a particle counter apparatus), such as an electrometer or a condensation particle counter as further described herein. For example, a number of the particles of the selected class is determined A "number" can in turn be understood to mean directly a number of a limited quantity of the selected class. This may be the case in particular if the particles of the selected class are made available, for example, in a closed vessel or if the selected class is closed in another manner.

Alternatively, or additionally, to the determination of the absolute number of particles of the selected class, however, it is also possible in turn for a variable correlating directly to the number to be used, for example a particle flow rate. This is especially expedient if the selected class is continuously made available, for example, in the form of a particle flow of the selected class being made available continuously. In this case, a particle flow rate, that is to say, for example, a number of particles flowing through a flow pipe per time unit, a volumetric flow rate or the like can be stated as the number. It is possible in principle for all known detection or counting methods to be used, for example, the methods known in the art. Although as previously discussed herein, some methods may have benefits over others.

In the other path 312, the class of particles is subjected to a filter apparatus to filter the class of particles (e.g., some particles will penetrate through the filter while others will not, depending on the morphology of such particles) (block 332). The filter apparatus may be any filter apparatus having a defined structure (e.g., known properties) such that particles in the class with different morphologies have corresponding different penetration levels therethrough. For example, any uniform or non-uniform filter which can give repeatable penetration measurements for like particle samples may be used. Further, for example, in at least one embodiment, any uniform filter allowing for penetration through the filter in the range of 0.0001% to 99.999% and which penetration values can be reliably measured may be used (e.g., penetration of about 1% or greater, about 5% or greater, about 95% or less, or about 99% or less). For example, depending on the size of the particles being characterized, different filters may be used (e.g., a system may be set up to provide for ease in filter access to allow for substitution of different filters). However, each of such filters will have different correlation data associated therewith; such correlation data providing the particular filter's relationship between penetration levels through such a filter by particles with different morphologies (e.g., agglomerates versus spheres, or agglomerates with different fractal dimensions, or nanotubes or nanowires with different lengths) and the corresponding morphology parameters defining such particles that penetrate the filter apparatus. The correlation may be used to determine the morphology characteristics of the particles in the class that penetrate the filter.

For example, the filter apparatus may be a screen filter (e.g., formed of a stainless steel material or any other suitable material), may be one filter, or more than one filter in combination with one another, may be a fibrous filter (as, for example, described in Kim et al. (2009), or Lange et al. (1999)), may be a membrane filter (e.g., a filter formed of polymer or metallic films with pores), or may be any other suitably defined filter. For example, the filter may be a filter available from TSI under the trade designation TSI 3040 Diffusion Screen, which is made of 635-mesh type 304 stainless steel. The screen wire of such a Screen is about 20 µm in diameter and the opening dimension is also about 20 µm. For example, such a filter has a highly regular and homogeneous structure. This provides ability to achieve repeatable filtration results and ensure the filtration model is a faithful representation of the actual filter.

Figure 5A:
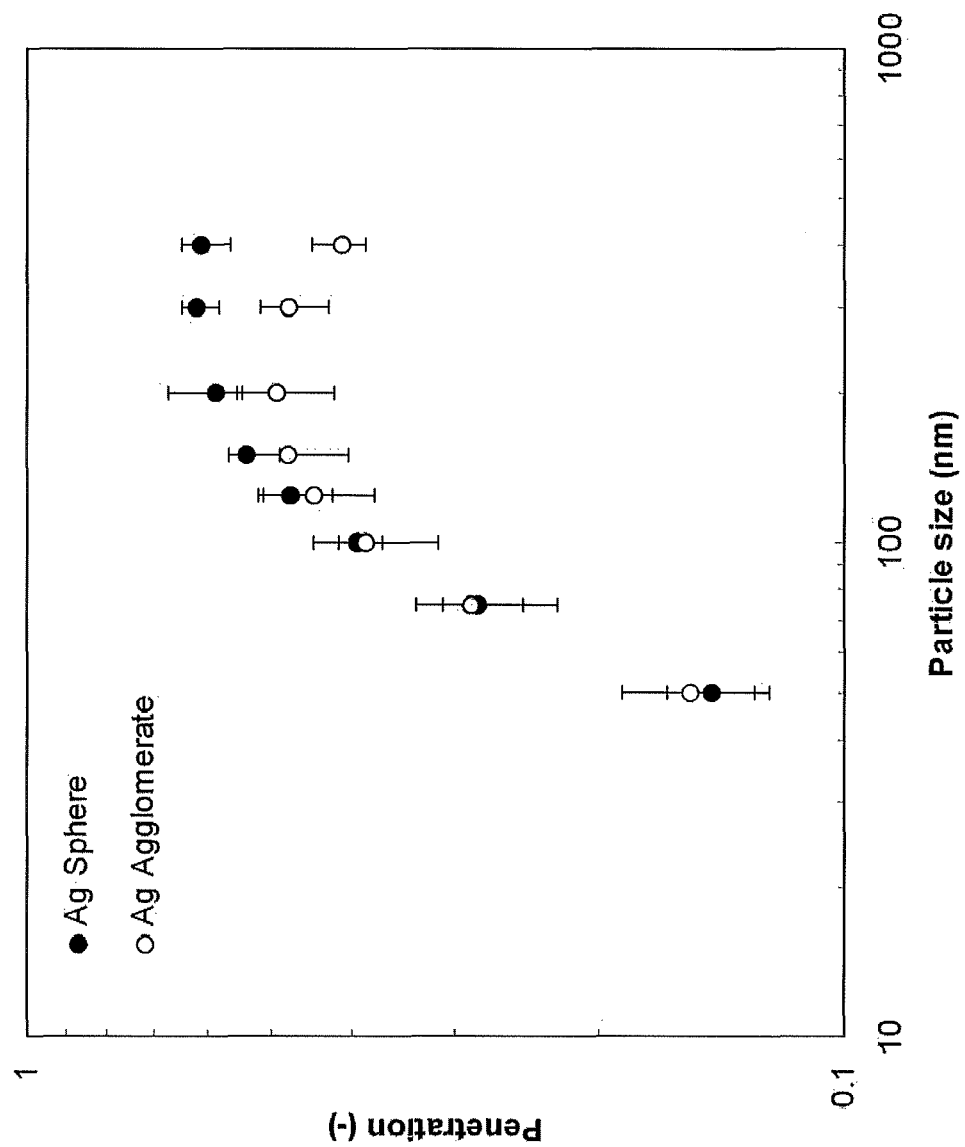
FIG. 5A is an illustration showing the fractional penetration for silver spheres and agglomerates through a filter (e.g., a Diffusion Battery Screen filter).
Figure 7:
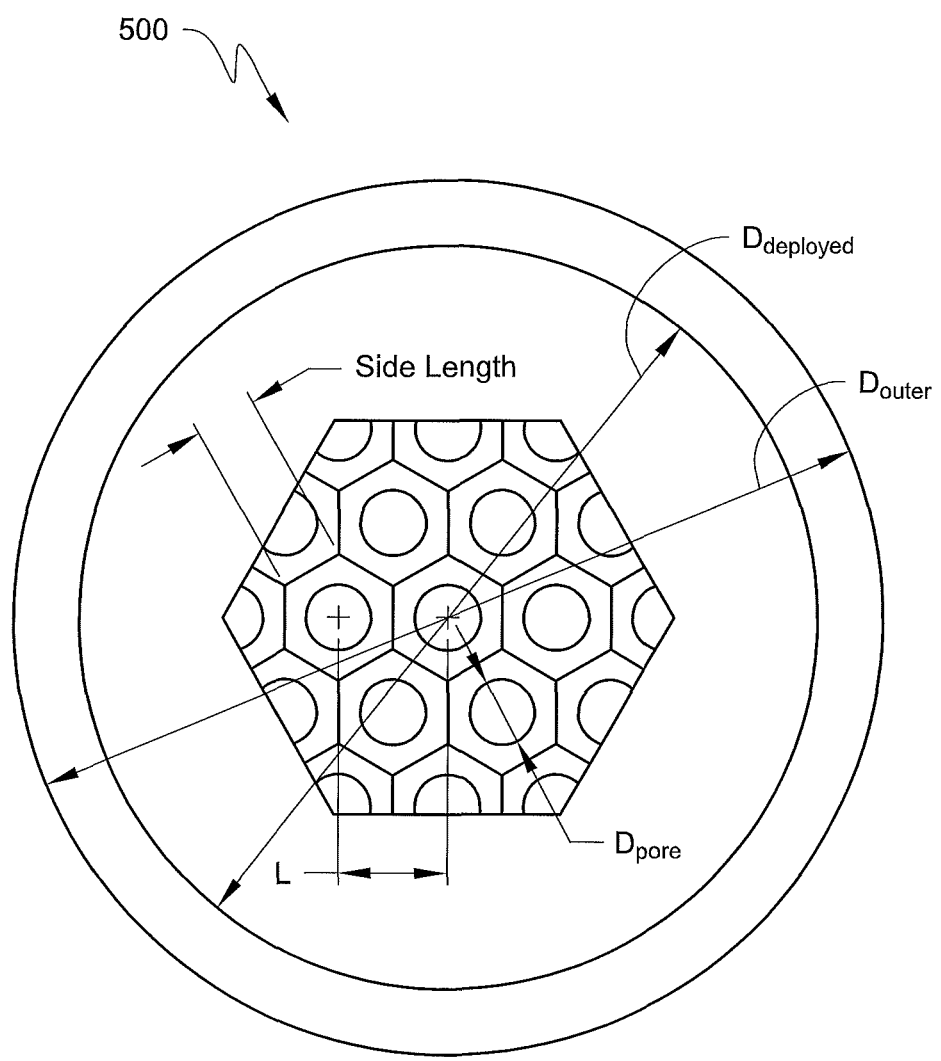
FIG. 7 is an illustration showing an exemplary illustration of a micro-pore filter that may be included in the filter apparatus described herein.

Further, the filter apparatus may be a multi-micro-orifice plate filter (e.g., a filter plate with multiple pores). One exemplary plate filter 500 is shown in FIG. 7. For example, the porosity of the plate filter may be greater than 0.001 and/or may be less than 0.999 (e.g., may be greater than 0.01 and/or may be less than 0.5, such as, for example, 0.05). For example, the pore diameter (Dpore) of the plate filter (e.g., that includes a hexagonal pattern of pore structures with pores at the center thereof, such as a hexagonal lattice structure with pores) may be greater than 0.005 µm and/or may be less than 100 µm (e.g., may be greater than 0.1 µm and/or may be less than 10 µm, such as, for example, 1 µm). For example, the distance between the center of two pores (L) of the plate filter may be greater than 0.005 µm and/or may be less than 100 µm (e.g., may be greater than 0.1 µm and/or may be less than 5 µm, such as, for example, 4.3 µm). Still further, for example, the outer diameter (Douter) of the plate filter may be greater than 1 mm and/or may be less than 1000 mm (e.g., may be 50 mm) and have a deployed diameter (Ddeployed) with a nozzle providing the particles that may be greater than 1 mm and/or may be less than 900 mm (e.g., may be 45 mm). Yet further, the side length of the reference hexagon of the hexagonal pattern of the plate filter may be greater than 0.008 µm and/or may be less than 100 µm (e.g., may be greater than 0.1 µm and/or may be less than 10 µm, such as, for example, 2.5 µm). One will recognize that various uniform pore pattern structures defining pores may be used to provide a multi-micro-orifice plate filter (e.g., non-hexagonal, pores in plate, etc.) and the scope of the present description is not limited to only those multi-micro-orifice plate filters described herein. However, even if the pores are not uniformly distributed or the pore sizes are not uniform, such filters may provide filtration results to determine particle parameters. Further, filtration experiments may be performed for silver spheres and agglomerates using a Diffusion Battery Screen filter available from TSI under the trade designation TSI 3040 Diffusion Screen. The fractional penetration is plotted in FIG. 5A as a function of the mobility size of the challenging particles. It can be seen that the penetration for agglomerates is lower than that for spheres when the mobility size is above 150 nm. As such, these results show that such filters can be used to determine the particle morphology.

In one or more embodiments, the filter apparatus may be required to meet certain requirements and/or be selected from a broader group of filter apparatus based on one or more criteria or tests. For example, filter apparatus may be selected from a group of filters based on the pressure drop of such filters. For example, with respect to the selection of one or more Nuclepore® filters (e.g., such selected filters being able to provide statistically reliable results from the penetration tests described herein and to obtain particle maximum length and/or fractal dimension as described herein), a pressure drop criteria for clean filters may be used to detect there suitability to provide statistically reliable results. For example, if the pressure drop of certain filters does not meet the pressure drop criteria, then such filters would not be used. For example, the pressure drop of such clean filters may be determined for a particular face velocity (e.g., 5 cm/s) as measured by using a Baratron manometer (available from MKS Instruments, Andover, Mass., USA). For example, with respect to 1 and 3 µm pore diameter filters if the pressure drop measured is within a range of 3.3-3.9 and 1.03-1.07 inch-$H_2O$ at 5 cm/s face velocity, respectively, then such filters may be effectively used in the penetration tests described herein. In the selected range of pressure drop, the defined total penetration and the corresponding particle maximum length and/or fractal dimension may provide an uncertainty less than 5%. For example, such criteria with respect to Nuclepore® filters may result in not using or excluding about 30% (n=120, 3 different packs) and 8% (n=30, 2 different packs) of 1 and 3 µm pore diameter filters, respectively, due to the measured pressure drop being outside the range of the predefined pressure drop. Of course, the exclusion rate may vary from filter pack to filter pack and/or depending on the filter type or parameter used to select or exclude such filters from a group of filters.

Figure 5B:
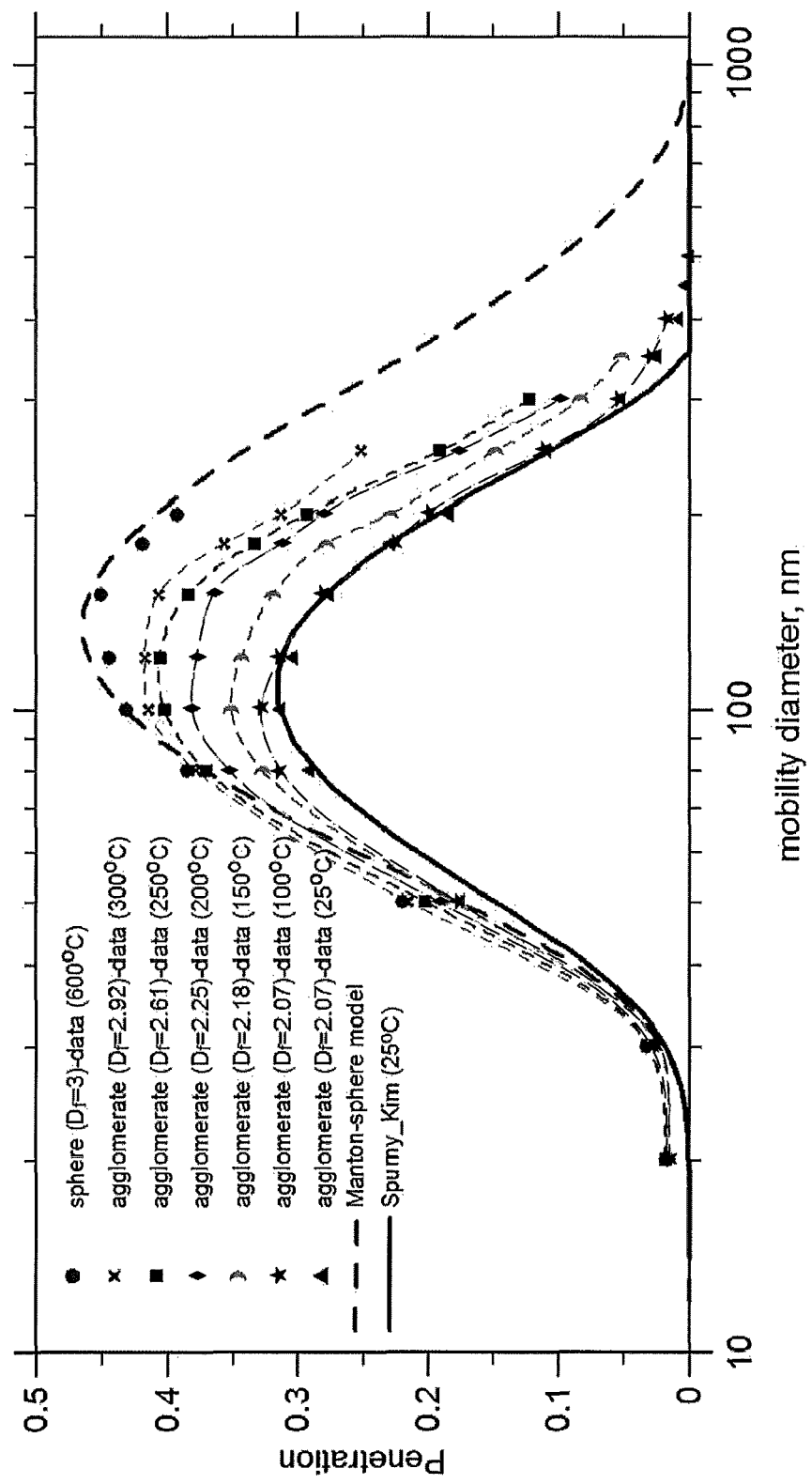
FIG. 5B is an illustration showing the fractional penetration for silver spheres and agglomerates through a filter (e.g., a micro-pore filter).

Further, additional other modeling and filtration experimentation may be performed for silver spheres and agglomerates as shown in FIG. 5B (e.g., using a Whatman®-Nuclepore® filter which has a pore diameter of 1 μm, an outer diameter of 47 mm, a porosity of 0.16, and a thickness of 11 μm). The fractional penetration is plotted in FIG. 5B as a function of the mobility size for different fractal dimension silver particles at a particular face velocity (e.g., 5 cm/s). Also, model estimated curves for different fractal dimension silver particles at the face velocity are also provided (e.g., Manton-sphere model curves and a Spurny-Kim model curve). It can be seen that the penetration for agglomerates increases as fractal dimension increases, with the most penetration being by the spheres (e.g., the penetration difference through a 1 μm pore diameter filter of spheres versus loose agglomerate may be as high as 10% to 30%, for example, at mobility diameters in the range of 100 nm to 300 nm). As such, these results also show that such filters (e.g., the penetration therethrough) can be used to determine particle morphology (e.g., differentiate between spheres and agglomerates, differentiate between agglomerates having different fractal dimensions, provide correlation information to determine such particle morphology, etc.).

Still further, face velocity may be a parameter that also may be used in determination of particle morphology. For example, the results shown in FIG. 5B were based on a face velocity of 5 cm/s and such results may be used in providing correlation information between fractal dimension of agglomerates and penetration, either directly or indirectly. However, such penetration curves or filtration efficiency curves may be provided for varied face velocities (e.g., a plurality of face velocities) to enhance correlation information between particle morphology and penetration, for example, between fractal dimension of agglomerates and penetration of such agglomerates through a defined filter. In such a manner, measurement uncertainty can be reduced and more structural parameters can be determined (e.g., fractal dimension, maximum length, effective density, etc.). Further, such face velocity information may be used to correct model parameters such that the models are enhanced.

Figure 8:
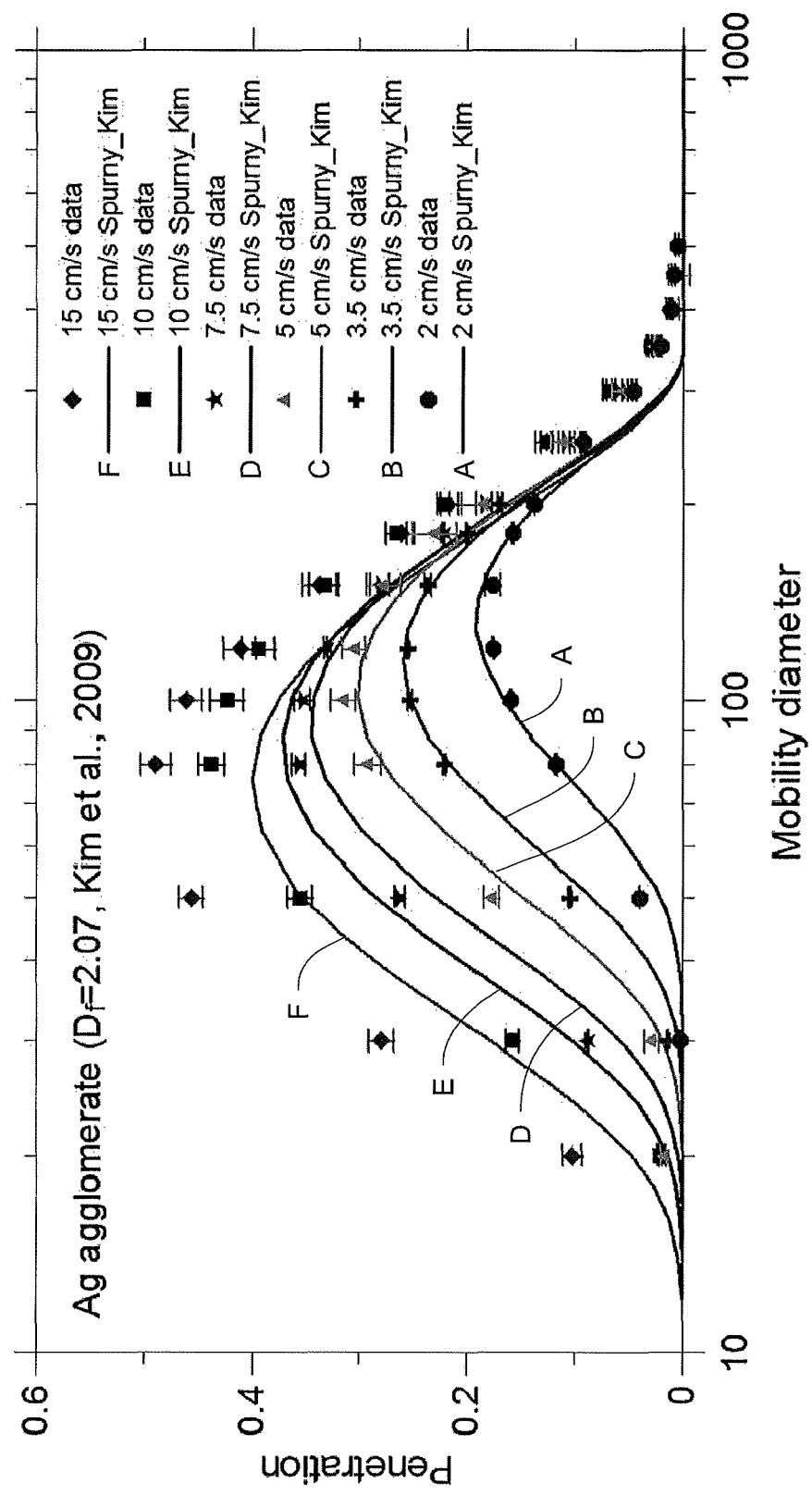
FIG. 8 shows an illustration of the penetration differences of the same agglomerates through a defined filter (e.g., a micro-pore filter) at different face velocities.

As shown in FIG. 8, additional modeling and filtration experimentation may be performed for silver agglomerates (e.g., agglomerates having a fractal dimension of 2.07 (e.g., using a Whatman®-Nuclepore® filter which has a pore diameter of 1 μm, an outer diameter of 47 mm, a porosity of 0.16, and a thickness of 11 μm). The fractional penetration of the agglomerates is plotted in FIG. 8 as a function of the mobility size for different face velocities of the silver agglomerates (e.g., face velocities of 2 cm/s; 3.5 cm/s; 5 cm/s; 7.5 cm/s; 10 cm/s; and 15 cm/s). Further, a model defined by Spurny-Kim as further described herein was used to provide expected modeled data. It can be seen that the model predicts penetration very well for face velocities less than or equal to 7.5 cm/s. For face velocities over 7.5 cm/s, the effect of alignment leads to the model providing an underestimation of particle penetration through the defined filter. As such, face velocities less than 10 cm/s appear to prevent the agglomerate alignment effect from tainting the determination of particle morphology (e.g., such as for agglomerates having a fractal dimension between 2 and 3 and electrical mobility sizes less than 300 nm). As such, these results also show that face velocities may be used to reduce measurement uncertainty (e.g., allow adjustment of model to better measure particle morphology, such as fractal dimension, etc.).

The filter apparatus preferably provides a spread of different penetration values for the various types of particles or particles with different morphologies being characterized. As such, the filter apparatus should not be a high efficiency filter relative to the particles being characterized. In other words, at least a certain percentage of the particles should be allowed to penetrate the filter apparatus (e.g., a percentage greater than about 0.0001%, a percentage greater than about 1%, a percentage less than about 99%, a percentage less than about 99.999%, a percentage greater than about 10%, a percentage greater than about 20%, or a percentage less than about 90%).

The screen filter may be formed of any suitable material. For example, a screen filter may be formed of stainless steel or aluminum. A fibrous filter may be formed of cellulose, glass, or quartz fibers. Further, a membrane filter may be formed of polymer, sintered metal, or ceramic.

For example, if a screen filter is used, wire of the screen filter may have a diameter in the range of about 500 nm to about 100 μm, and the opening dimension of the filter may be in the range of about 500 nm to about 100 μm. For example, if a fibrous filter is used, the fiber size may be in the range of about 5 nm to 100 μm with porosities in the range of 0.1 to 99 percent. Further, for example, if a membrane filter is used, the pore size may be in the range of about 5 nm to about 100 μm. The solid fraction of such filters may be in the range of 0.1% to 99.9% (e.g., may be in the range of 1% to 70% (i.e., solid fraction referring to the fraction of solid material in the filter compared to the total volume of the filter).

Further in path 312, a filtered particle concentration indicative of the particles of the class which penetrates the filter apparatus is determined (block 334). The filtered particle concentration may be determined with use of a particle detector apparatus such as described in path 310 (e.g., such as an electrometer or a condensation particle counter as further described herein). For example, a number of the particles of the selected class is determined which have penetrated the filtered apparatus. This may in turn be understood to mean directly a number of a limited quantity of the selected class, which may be the case in particular if the particles of the selected class are made available, for example, in a closed vessel or if the selected class is closed in another manner. Alternatively, or additionally, to the determination of the number of particles of the selected class, it is also possible for a variable correlating directly to the number to be used, for example, a particle flow rate. This is especially expedient if the selected class is continuously made available, for example, in the form of a particle flow of the selected class being made available continuously. In this case a particle flow rate, that is to say, for example, a number of particles flowing through a flow pipe per time unit, a volumetric flow rate or the like can be stated as number. It is possible in principle for all known detection or counting methods to be used, for example, the methods known in the art. Although as previously discussed herein, some methods may have benefits over others.

With the total particle concentration of the class of particles being known (block 320) and the filtered particle concentration of the particles of the class which penetrated the filter apparatus being known (block 334), at least one morphological parameter based on the fraction of particles of a class penetrating the filter apparatus may be determined (block 360) (e.g., a fractional penetration level defined as the ratio of the filtered particle concentration to the total particle concentration may be determined and the at least one morphological parameter may be determined based on the fractional penetration level). The at least one morphological parameter may include, for example, at least one item of information (e.g., fractal dimension) about an agglomerate state of the fraction of particles of the class of particles penetrating the filter apparatus.

The process of determining the at least one morphological parameter based on the fraction of particles of a class penetrating the filter apparatus uses information correlating the fractional penetration of particles through the filter apparatus to one or more morphological parameters (block 350). As described herein, a morphological parameter includes morphological information about an agglomerate state of the particles. This morphological parameter can include, for example, one or more numbers, vectors, matrices or else classifications into morphological classes. In at least one embodiment, the at least one morphological parameter includes at least one of the following items of information: information about a categorization into morphological agglomeration classes, in particular a distinction between loose agglomerates, partially aggregated particles and aggregates; a number of primary particles; a fractal dimension of the particles, particle maximum length, a shape factor, etc.

It is possible to establish an at least largely unique relationship between the fractional penetration through a defined filter and the morphological parameter. Such a relationship may depend on an accurate understanding of both the filtration process and the morphological parameters of the particles. This relationship can be obtained, for example, with the use of empirical, semi-empirical or analytical or theoretical considerations. By way of example, this relationship can be recorded in the form of a single-variable function, a multi-variable function, a graph, a value table, an electronic table or in similar form and used in the process of determining a morphological parameter for the particles penetrating the filter apparatus. As used herein, correlation information may take any one of such forms, or any other suitable form.

As likewise indicated above, it is possible, for a known relationship between fractional penetration of particles in the class and the morphological parameter to be used. This known relationship can, for example, include at least one correlation function (also referred to as calibration function or correlation information herein) which is determined by empirical, semi-empirical or analytical means. A correlation function is, however, not necessarily to be understood here as a function in the conventional meaning, but the term can also include, for example, recorded calibration values, for example calibration values recorded in one or more tables or matrices and/or multi-variable curves of calibration functions, for example, multi-variable curves which are parameterized with the morphological parameter (e.g. the fractal dimension of the particles).

It is in particular possible for the known relationship, which is used in the calibration function, to be determined for example by off-line methods. It is, however, alternatively or additionally, also possible to determine the relationship by means of on-line methods. Since the known relationship, which is ascertained in this manner, can subsequently be used in on-line methods, the herein-mentioned cost and time advantages of the method(s) described herein are not decreased. For example, the known relationship can be determined using a plurality of test particles, wherein, for example, the morphological class and/or the fractal dimension of the test particles can be determined in an off-line method, in particular an imaging method. The fractional penetration of the test particles can subsequently be determined using a method according to the present disclosure, and, for example, the fractal dimension can be ascertained by way of the relationship between the fractional penetration of the particles through the filter apparatus using the obtained knowledge concerning the morphological class. The relationship can be ascertained, for example, using fit functions, curves, or the like.

According to one embodiment, a correlation can be established between particle structural parameters (e.g., fractal dimension) for certain particles and the penetration of such particles through the defined filter apparatus measured by filtration experiments. For example, such a correlation takes the particle structural parameters, flow parameters (e.g., face velocity, media velocity, etc.), and filter parameters as input, and gives the particle penetration as output. The particle structural parameters may include mobility diameter, particle length, fractal dimension, primary particle size, dynamic shape factor, density, etc. The flow parameters may include the velocity of the gas or liquid in flow at the face of the filter as well as through the filter, as well as the temperature, pressure, viscosity and density of the gas or liquid. The filter parameters may include the wire, fiber or pore size, solid fraction, filter thickness, etc. For example, the correlation information may include analytical, empirical and semi-empirical equations and can be calibrated by filtration experiments using spheres, nanotubes, loose agglomerates, and sintered agglomerates with known structural parameter values. Such structural parameter values of the particles used in the calibration can be measured by techniques such as electron microscopy, aerosol particle mass analyzer, etc. The penetration fractions can be measured from filtration experiments (e.g., using the apparatus described herein operating on the particles with known structural values). Such correlation data can ensure that the correlation gives correct results for particles with different morphologies and structures.

For example, such correlation data may include the correlation between a certain structural parameter (e.g., fractal dimension) and various filter penetration versus mobility size curves (e.g., obtained through calibration as indicated above). Further, such curves may be provided for a plurality of face velocities. Then, to measure the certain structural parameter (e.g., fractal dimension) of a class of test particles using the correlation data, one can perform the filtration experiments to obtain a penetration versus mobility size curve for the test particles. This curve can be compared with those from the correlation data, and one can determine the best match (e.g., software algorithms may be used to provide such analysis). The corresponding value of the structural parameter (e.g., fractal dimension) is then the value for the test particles. As indicated, the fractal dimension, for example, can be the structural parameter measured using the correlation data.

In other words, the process may include the determination of more than one morphological parameter in a row. For example, it is possible using a known fractional penetration through a defined filter for a particular class of particles to conclude that the particular specific morphological class of particles is present, for example, a loosely agglomerated chain-type or branched state, or, for example, whether the particles are nanotubes. This can be done for example, as explained herein, when it is known for a pre-specified fractional penetration that such penetration is representative of a specific morphological class. It is then possible to determine further morphological structural parameters using the correlation data. Calibration functions can be used for this purpose, for example, as explained herein. It is possible, for example, to ascertain a fractal dimension for such particles by way of a calibration function, which is valid for the ascertained morphological class.

The method described herein enables an on-line characterization of the particle totality since, on the basis of the morphological parameter which can be determined on-line, other characteristic variables (referred to below as "target variables") may be determined, such as surface area, volume, primary particle size and number per agglomerate or aggregate, internal porosity and/or an agglomerate or aggregate porosity, apparent density, agglomerate or aggregate density or the like. It is thus possible to determine various structural parameters, in particular of nanoscale agglomerates, from the measurement variables, which can preferably be done without the aid of offline analysis. In this manner, in particular toxicities, environmental compatibility, reactivities or similar properties of the particles can be predicted or estimated much better than is the case with conventional methods. Since the measurement can be carried out on-line, the proposed method can, in addition, be implemented without problems in a quick and cost-effective manner in various available measurement apparatuses, for example, for open-loop and/or closed-loop process control (e.g., wherein measurements can be used to control a process being performed).

The exemplary proposed method 300 in its basic form can be developed further advantageously in a variety of ways. For example, the method 300 illustrated herein describes the determination of the morphological parameter for the respectively selected class. However, the method steps can also be repeated. This is useful in particular for a so-called scan, that is to say a method in which different classes with different mobilities $d_m$, i.e., mobilities which at least do not coincide completely, are selected one after the other. For these different classes, the morphological parameters are then determined in each case according to the exemplary method. To this end, it is possible to carry out the various steps of the method repeatedly.

As illustrated above, the proposed method can be used in particular as an on-line method, that is to say a method which provides results in near real-time in a process without the process (for example a manufacturing or production method) having to be interrupted significantly for this purpose. Nevertheless, the proposed method can be expanded optionally by off-line measurements. This can be advantageous, for example, for carrying out reference measurements, for ascertaining the relationships (illustrated above) or for occasionally monitoring the plant. To this end, the method may include a sampling process in which a quantity of the particles of a selected class is removed. By way of example, it is possible to remove particles for each selected class or also only for one or more specific selected classes. The quantity of removed particles can be investigated in an alternative characterization method, in particular an off-line characterization method.

The characterization method can in particular be an imaging method and/or a chemical analysis method. It is possible in this manner to ascertain, for example, morphological parameters such as morphological classes, primary particle sizes or the like using an optical microscopy method, a scanning electron microscopy method, a transmission electron microscopy method, an atomic force microscopy method or other known imaging methods or combinations of such imaging methods.

In addition to the methods described herein, furthermore a system for characterizing a totality of particles is provided. The system can be designed in particular for carrying out a method according to one or more of the embodiments described herein. With respect to possible embodiments, the system may include a controller apparatus. For example, the controller apparatus can, for example, be in the form of a centralized or decentralized controller and can, for example, comprise an electronic controller, in particular a data-processing machine. The data-processing machine can comprise, for example, a microcomputer and/or a personal computer, including one or more processors, memories, input and output means and/or similar appliances which are usually present in data-processing machines. Accordingly, one or more programs may be executed to perform control of the process or implementation of any functionality described herein (e.g., including determination processes, such as concentration determination and/or determination of morphology parameters).

According to the methods described herein, the system may include various components (e.g., detectors, classification apparatus, controllers, etc.). Such system components can be in the form of separate or directly connected elements (for example, connected to one another via a line system). The components can, however, also be fully or partially integrated with one another, such that for example, the classification apparatus and a particle detection or counter apparatus can be designed fully or partially with identical components. The calibrator apparatus may include a data-processing machine, since the tasks of the calibrator apparatus are in particular in the area of data processing and analysis. The calibrator apparatus can furthermore also comprise interfaces by means of which, for example, input and output operations can be undertaken, wherein, for example, morphological parameters (for example, fractal dimension) or target variables derived therefrom can be queried (e.g., the calibrator apparatus may be provided at least in part by the controller apparatus).

As described herein, the system may include a line system. This line system is intended to be designed for guiding a flow of the particles, in particular a volume flow and/or mass flow of the particles. For this purpose, the particles can be present, as explained above, in the form of gas-borne particles, in particular as aerosol. By way of example, a carrier gas can be used. The components of the system are intended to be connected to the line system. For example, the classification apparatus in the line system can be connected upstream of the particle detection apparatus and the filter apparatus. In addition, the line system can, of course, include one or more gas inlets, for example, for introducing the primary particles and/or one or more carrier gases. Furthermore, the line system can also include measurement and/or control devices, for example, measurement devices for determining a volumetric flow rate, pumps, flow meters, flow controllers, valves or the like. At least in one embodiment, the line system of WO 2009/098215 A1 is connected to line system components for carrying out the filtration functionality described herein. As such, the determination of morphological information using a filtration apparatus as described herein may be implemented partially or with modification of the system described in WO 2009/098215 A1 (e.g., the addition of one or more programs to control and/or determine morphological parameters, the addition of paths for determination of filtered particle concentrations and/or total particle concentration, etc.).

The two paths of the system represented in the method 300 by paths 310, 312 are, at least in one embodiment, arranged in parallel branches of the line system. Here, a branching ratio between a first partial flow rate through a first path, in which a total concentration is determined, and a partial flow rate through a second path in which a filtered particle concentration is determined, can be known or can be set. At least in one embodiment, the first and the second partial flow rates are equivalent. To, for example, ensure a flow equalization between the first partial flow rate and the second partial flow rate and the total flow rate of the particles flowing through the line system, it is possible for the line system to additionally include at least one bypass line, wherein the bypass line is designed for guiding a bypass flow. It is thus possible to adjust the individual partial flow rates in an efficient manner.

As described above within the framework of the method 300, it can occasionally be expedient to carry out an off-line analysis, in addition to an on-line characterization of the totality of the particles. The system can accordingly furthermore include at least one sampler, in particular a sampler which is connected to the line system. The sampler can be designed in particular for removing a quantity of the particles of a selected class and introducing them into an alternative characterization method, in particular an imaging method. The sampler can in principle use any desired way of removing particles. By way of example, the samplers may be used for depositing particles, for example, on a substrate. They can be deposited, for example, on one or more transfer substrates which are subsequently introduced into the imaging method.

Figure 2:
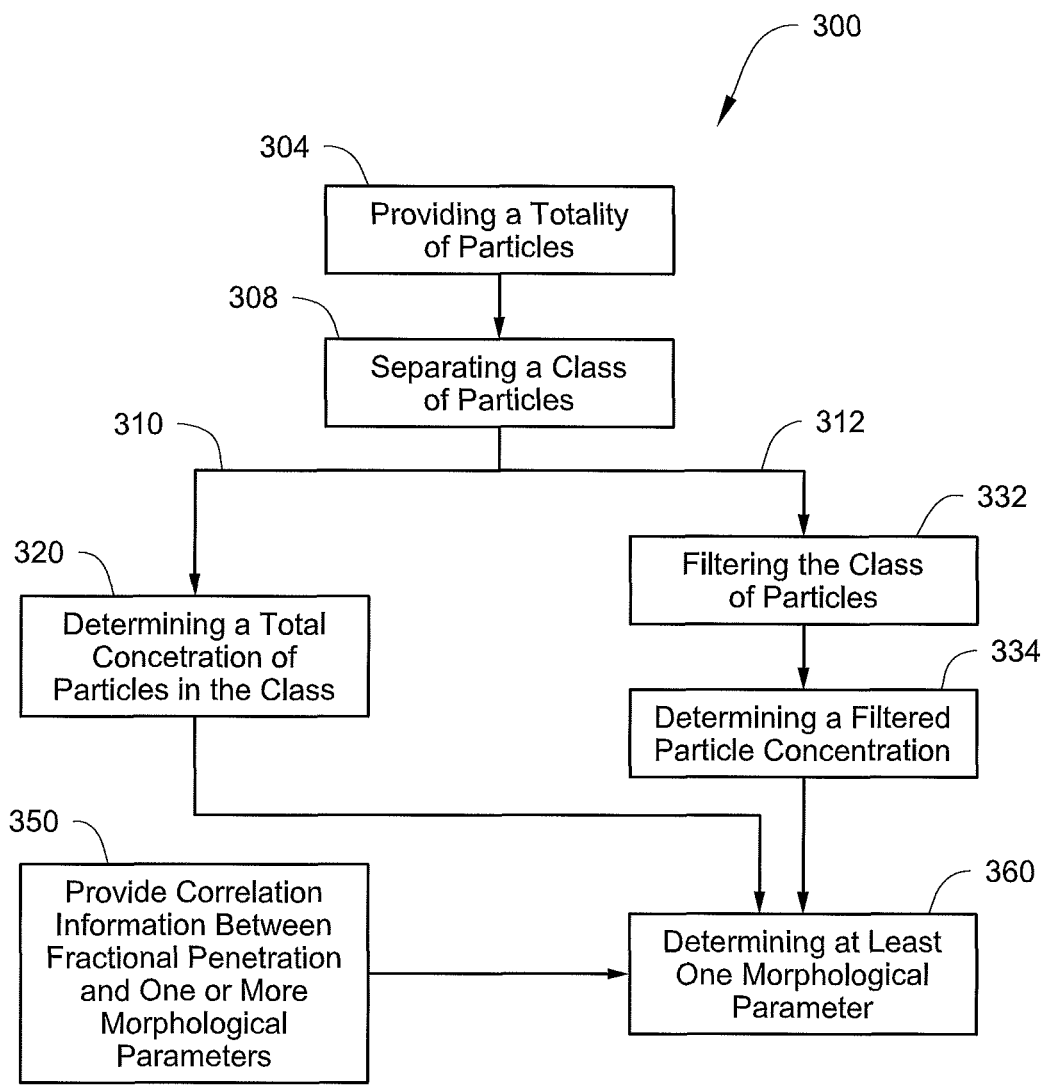
FIG. 2 is a block diagram of an illustrative process of a characterization method that may be implemented using the system of FIG. 1.

One exemplary embodiment of a system 100 for characterizing a totality of particles is shown in FIG. 1. The system 100, for example, may include a classification apparatus 124 to select a class of the totality of particles having a defined mobility, a first particle counter apparatus 170 positioned in a first path 160 of the system 100 for use in determining total particle concentration of a class of particles, a filter apparatus 180 positioned in a second path 162 of the system 100 (e.g., wherein the filter apparatus 180 is defined such that particles of a class with different morphologies correspond to different penetration levels therethrough), and a second particle counter apparatus 172 positioned in the second path 162 for use in determining a filtered particle concentration indicative of particles of a class which penetrate the filter apparatus 180.

Further, the system 100 may include a calibrator apparatus (e.g., which may be provided, at least in part by controller apparatus 120) configured to determine at least one morphological parameter based on the fraction of particles of a class penetrating the filter apparatus 180, wherein the fraction is determined as a function of the total particle concentration and the filtered particle concentration (e.g., the calibrator apparatus may be configured to determine at least one morphological parameter based on a fractional penetration level defined as the ratio of the filtered particle concentration to the total particle concentration). Generally, for example, the at least one morphological parameter includes at least one item of information (e.g., fractal dimension) about the particles of the class of particles penetrating the filter apparatus 180.

FIG. 1 schematically illustrates the exemplary embodiment of the system 100 for characterizing a totality of particles. It is assumed for simplicity herein with respect to the system 100, without restricting the possibility of further embodiments, that the totality of particles refers to particles of an aerosol.

In the exemplary embodiment illustrated in FIG. 1, the system 100 has a common line system 112, to which aerosol can be supplied via an aerosol inlet 114. The aerosol inlet 114 can have various designs, so that, for example, different connections for carrier gases, particles, aerosols or similar can be provided. The particles or the aerosol are sucked through the line system 112 using a pump 116 which is regulated, for example, at a constant volumetric flow rate. It can be regulated, for example, using a mass flow controller (MFC) 118. The flow rate can, for example, be adjusted by way of controller apparatus 120 of the system 100, to which, for example, measurement signals of individual or all of the components illustrated in FIG. 1 can be delivered and which can output control and/or regulating signals to individual or all of the components of the system 100 illustrated in FIG. 1. This controller apparatus 120 can, for example, include a microcomputer and/or a personal computer (e.g., one or more processors suitable for executing instructions or programs), as well as memory and any other suitable input and output mechanisms.

In the line system 112, a charge state generator 122 is arranged, which is connected to the aerosol inlet 114 via the line system 112. The charge state generator 122 can, for example, be in the form of a bipolar charging source and can, for example, be equipped with a radioactive source. However, other embodiments are also possible as described herein.

The charge state generator 122 is connected to a classification apparatus 124 again via the line system 112. This classification apparatus 124 is, in turn illustrated only symbolically in FIG. 1. In the exemplary embodiment, this classification apparatus may be a differential mobility analyzer (DMA), that is to say a classification apparatus 124 which can select a class with a pre-specified mobility $d_m$ from the aerosol, for example, by setting a particular aperture geometry and/or a voltage and/or an electric field. Selection of the class can, for example, in turn be controlled by the controller apparatus 120 such that the mobility $d_m$ which is selected can be pre-specified by the controller apparatus 120. In a similar way, it is possible for mobility scans to be carried out, for example, that is to say scans in which different classes are selected one after the other. Such a scan can be controlled, for example, in the classification apparatus 124 itself and/or control can again be pre-specified by the controller apparatus 120. In one or more other embodiments, it is also alternatively or additionally possible, however, for other types of classifiers to be used, such as diffusion classifiers (e.g., diffusion separators), particle mass spectrometers, nano-impactors or similar classifiers or combinations of classifiers.

The classification apparatus 124 is connected to first and second parallel paths 160, 162 in the line system 112.

A partial line 126 which is connected to a sampler 128 branches away from the line system 112 between the classification apparatus 124 and the first and second parallel paths 160, 162. The sampler can, for example, be in the form of a nanoparticles aerosol sampler for enabling samples for an off-line characterization of the selected class or a plurality of selected classes of the aerosol. To this end, the sampler 128 can, for example, include one or more sample carriers to which one or more particles of one or more classes of the aerosol can be applied, for example, in order to be subsequently introduced into an imaging method. The partial line 126 can, just like, for example, one or more of the remaining sections of the line system 112, be equipped with one or more valves for controlling, for example, a sampling operation. The valves can, in turn, be operated via the controller apparatus 120, with the result that, for example, the sampling can also be controlled by way of the controller apparatus 120.

By the first path 160, the classification apparatus 124 is connected to the first particle counter apparatus 170 positioned in the first path 160 of the system 100 for use in determining total particle concentration of a class of particles. By the second path 162, the classification apparatus 124 is connected to the filter apparatus 180, which is connected to the second particle counter apparatus 172 positioned in the second path 162 of the system 100 for use in determining a filtered particle concentration indicative of particles of a class which penetrate the filter apparatus 180.

The filter apparatus 180 includes a filter 186 (e.g., a replaceable filter or a filter that can be substituted for another) as well as a filter holder 184 (e.g., compatible with more than one filter type). The filter holder 184 may be provided by any suitable structure for holding the filter 186.

The ratio of the partial flow rates through the two paths 160, 162 is, at least in one embodiment, known, or can be set. This can be done, for example, by way of appropriate apertures and/or valves, which can be adjusted, for example, again by way of the controller apparatus 120. At least in one embodiment, the partial flow rate through the two paths is adjusted such that they are equal.

The exemplary embodiment illustrated in FIG. 1 furthermore provides one or more bypass lines 138 which guide a bypass flow to the pump 116 past the first and second particle counter apparatus 170, 172. In the exemplary embodiment illustrated in FIG. 1, the first and second particle counter apparatus 170, 172 are connected, at their downstream side, again to the bypass line 138, so that the partial flow flowing through the first path and second path is sucked through the counter apparatus 170, 172 by way of the pump 116.

The first and second particle counter apparatus 170, 172 can, for example, as illustrated herein, include an electrometer or a condensation particle counter (CPC), or any other suitable particle detection apparatus. Alternatively or in addition, the particle counter may also include a laser counter and/or another type of optical counter. Alternatively or in addition, the particle counter can also include at least one electrostatic counter which is designed for inferring a particle number and/or a particle flow rate from an electric current caused by charged particles. Other types of counters or combinations of the counters mentioned and/or other counters can, of course, also be used. In one embodiment, a Faraday cup electrometer is used.

The particles are caused to flow through the line system 112 using the pump 116, which is adjusted to a constant volume flow rate, firstly through the charge state generator 122, which is connected upstream of the classification apparatus 124 (e.g. DMA) and brings the particles to an electrically defined charge state. As described herein, this can be a bipolar charging apparatus using, for example, a radioactive source.

Subsequently, the particles are classified into monodisperse fractions of equal size, i.e., of the same mobility, using the classification apparatus 124 which may operate, for example, in an electrostatic manner. The fractionation may be modified, for example, by varying the electric voltage or the electric field, with the result that an entire size range or range of fractions can be measured alone or within the framework of a scan. The class or monodisperse particle fraction thus selected is subsequently brought to the parallel paths 160, 162.

The flow is divided and guided to the first particle counter apparatus 170 via the first path 160 and to the filter apparatus 180 via the second path 162. As described herein, the first counter apparatus 170 may be an electrometer suitable for counting particles to determine the total particle concentration of class of particles. Further, the filter apparatus 180 only allows a portion or fraction of the class to penetrate the filter apparatus 180 to be detected and counted via the second particle counter apparatus 172. As described herein, the second particle counter apparatus 172 may be an electrometer suitable for counting the fraction of particles of the class that penetrate the filter apparatus 180 to determine the filtered particle concentration. The ratio of the measurements of filtered particle concentration to total particle concentration of the class provides a fractional penetration level which correlates to one or more morphological parameters which can be determined by controller apparatus 120 (e.g., by operation of one or more programs or analysis of measurements and correlation information).

The determination of one or more morphological parameters may be carried out in a fully or partially computer supported manner, for example, again using the controller apparatus 120 of the system 100 in FIG. 1. To this end, this controller apparatus can, for example, comprise a data-processing machine, which can be appropriately equipped in terms of program technology. For the purposes of clarifying a possible embodiment for carrying out the determination of one or more morphological parameters, reference is made to FIG. 4A which shows a correlation between penetration through a defined filter apparatus and the type of particles penetrating such a filter apparatus. For example, particles of a class defined by a certain mobility diameter may be correlated to being spherical nanoparticles, agglomerated particles, or nanotubes depending on the fractional penetration level.

FIG. 4A shows off-line images of a spherical particle, agglomerates, and nanotubes which are selected as examples. These images may be obtained using imaging methods. As can be seen in the images of FIG. 4A, the agglomerates are merely in the form of loose linkages of approximately spherical partial particles, which are also referred to as primary particles. Depending on the type of the particle system used, the primary particles can, however, also have a different geometry, for example, a square geometry, a plate-type geometry, a rod-type geometry or the like. While in the case of a sphere as primary particles the diameter can serve as primary particle size, in the case of other geometries of the primary particles other variables characterizing the size of the primary particles must be used, such as an edge length. FIGS. 4A and 4B, as well as FIG. 5B, also shows such correlation between penetration and particle morphology.

Correlation information used in the system 100 relates the particle structural parameters and the fractional penetration of particles through the filter apparatus 180. A more detailed description of such an illustrative correlation is provided herein as an example. For example, the filtration in wire screen filters or fibrous filters can be described using the known single-fiber model. Particles may be captured by the fiber due to their Brownian diffusion motion, the interception effect, the inertial impaction, the electrostatic effect, and other less important mechanisms such as gravitational settling. The single-fiber efficiency due to interception ($E_R$), the efficiency due to diffusion ($E_D$), and the efficiency due to inertial impaction ($E_I$) may be expressed as (Wang and Pui, Filtration of aerosol particles by elliptical fibers: a numerical study, Journal of Nanoparticle Research 11, 185-196, 2009):

$$E_R = \frac{1+R}{2Ku}\left[2\ln(1+R) - 1 + \alpha + \left(\frac{1}{1+R}\right)^2\left(1 - \frac{\alpha}{2}\right) - \frac{\alpha}{2}(1+R)^2\right]; \quad (1)$$

$$E_D = 2.9Ku^{-1/3}Pe^{-2/3} + 0.624Pe^{-1}; \quad (2)$$

$$E_I = \frac{1}{(2Ku)^2}[(29.6 - 28\alpha^{0.62})R^2 - 27.5R^{2.8}]Stk; \quad (3)$$

where the parameters are defined as:

$$Stk = \frac{\rho_p d_p^2 C_c U_0}{18\mu d_f} \quad (4)$$

$$R = d_p/d_f \quad (5)$$

$$Pe = \frac{d_f U_0}{D} = d_f U_0 \frac{2\pi\mu}{kTC_c} d_p \quad (6)$$

$$Ku = -0.5\ln\alpha - 0.75 - 0.25\alpha^2 + \alpha \quad (7)$$

In the equations, $\alpha$ is the solidity or the packing density, $U_0$ is the face velocity, $\mu$ is the gas or liquid viscosity, $\rho_p$ is the particle density, $C_c$ is the slip correction factor, $D$ is the diffusion coefficient, $k$ is the Boltzmann constant, $T$ is the temperature, $d_f$ is the fiber or wire diameter. The parameter $d_p$ represents the particle size. It is the diameter if the particle is spherical. For a fractal-like particle, the values used in equations (4) to (6) are dependent on the particle morphology and structure. The fractal dimension is an important morphological parameter, which can be obtained from the correlation for a class of particles:

$$m = \beta(d_p)^{D_f} \quad (8)$$

where m is the particle mass, $\beta$ is a proportionality parameter, $d_p$ here is a certain characteristic size of the particle, and $D_f$ is the fractal dimension. The fractal dimension is 3 for solid spherical particles, and 1 for tubes or chain particles. The fractal dimension plays a role in calculation of different sizes for the particles.

An example of a mathematical description of agglomerates based on morphological parameters is the model by Vainshtein and Shapiro described in Vainshtein et al., "Mobility of permeable fractal agglomerates in slip regime," J. Colloid Interface Sci., 284:501-509 (2005). In this model, a fractal agglomerate is assumed to have a spherically symmetric porous structure with radially increasing porosity. The approximation of a porous sphere enables analytical treatment for the aerodynamics of fractal agglomerates otherwise excessively complicated. The flow field is described by the Stokes equation outside the agglomerate and by the Brinkman equations within the agglomerate. The solution of the flow field gives rise to the drag coefficient for the agglomerate, defined as the ratio $\Omega$ between the actual drag $F_d$ on the agglomerate and the Stokes drag on a sphere of equal outer diameter $d_c$, $$\Omega = \frac{F_d}{6\pi\mu d_c U}, \quad (9)$$

where $\mu$ is the viscosity and U is the relative velocity. Vainshtein and Shapiro (2005) introduced a porous Knudson number, $Kn_p$, to account for the gas rarefaction and slip within the agglomerate. Their solution gave rise to the drag coefficient as a function of the outer diameter $d_c$, primary sphere size $d_p$, and the fractal dimension $D_f$, $$\Omega = \Omega(d_c, d_p, D_f). \quad (10)$$

Using the relationship between the drag force and the electrical mobility (Hinds, W. C., "Aerosol technology: Properties, behavior, and measurement of airborne particles", Second ed. Wiley-Interscience, New York, USA, (1999)), the mobility diameter $d_m$ can be written as a function of $d_c$, $d_p$, and $D_f$. Conversely, $d_c$ can be computed when $d_m$, $d_p$ and $D_f$ are known, $$d_c = d_c(d_m, d_p, D_f). \quad (11)$$

The outer diameter $d_c$ can be considered as the effective interception diameter and may be used in Equation (5) to compute the interception efficiency.

The particle size in Equation (6) is the diffusional size, thus the mobility diameter should be used here. The Stokes number in Equation (4) can also be written as (see Kim, et al., "Structural Property Effect of Nanoparticle Agglomerates on Particle Penetration through Fibrous Filter," Aerosol Science and Technology, 43: 4, 344-355 (2009))

$$Stk = \frac{mC_c(d_m)U_0}{3d_m\mu d_f} \quad (12)$$

The particles coming out of the DMA are mostly singly charged. The electrostatic force can lead to particle capture by the fibers. The single-fiber efficiency for electrostatic image forces $E_q$, for a neutral fiber and a particle with charge q, based on experimental measurements with glass fiber filter, can be expressed as (Brown, "Air Filtration: An Integrated Approach to the Theory and Applications of Fibrous Filters," Pergamon, Oxford, U.K., 1993)

$$E_q = 1.5\left[\frac{(\varepsilon_f - 1)}{(\varepsilon_f + 1)}\frac{q^2}{12\pi^2\mu U_0\varepsilon_0 d_p d_f^2}\right]^{1/2} \quad (13)$$

where $\varepsilon_f$ is the relative permittivity (dielectric constant) of the fiber, q is the charge on the particle, and $\varepsilon_0$ is the permittivity of a vacuum.

Combining equations (1) to (13), one can compute the single-fiber efficiency $$E = E_D + E_R + E_I + E_q. \quad (14)$$

Then the penetration through the filter can be computed as $$P = \exp\left(-\frac{4\alpha E t}{\pi d_f(1-\alpha)}\right) \quad (15)$$

where t is the filter thickness. The correlation described here computes the penetration given the mobility diameter and the fractal dimension. Thus from filtration experiments using particles with known mobility diameters, the fractal dimension can be obtained by matching the experimental results and the correlation results. The above equations and constants used in the equations can be modified during calibration to ensure that the equations are effective for selected filter and different fractal-like particles. Once the fractal dimension is determined, the particle mass equation (8), the particle outer diameter equation (11), the dynamic shape factor which is directly related to the Stokes number equation (12), can all be determined as discussed above.

For example, as described, the correlation data for determining fractal dimension may include various filter penetration versus mobility size curves for different fractal dimensions. Then, to obtain the fractal dimension of a class of test particles using the correlation data, one can perform the filtration experiments to obtain a penetration versus mobility size curve (or curves in the case of a scan) for the test particles. Such curves can be compared with those determined as described above, and one can determine the best match (e.g., software algorithms may be used to provide such analysis) to determine fractal dimension value or values.

An example is described to combine the single-fiber filtration theory and the agglomerate theory by Vainshtein and Shapiro (2005) to form a technique to calculate the fractal dimension of agglomerates. The model of Vainshtein and Shapiro (2005) can be used to express the outer diameter $d_c$ as a function of the primary particle size and fractal dimension. On the other hand, the effective interception diameter can be computed from the filtration experimental results using the single fiber filtration theory. The fractal dimension which leads to the minimal discrepancy between the outer diameter $d_c$ and the interception diameter can be found. This value is considered to be the fractal dimension of the test particles.

Figure 6:
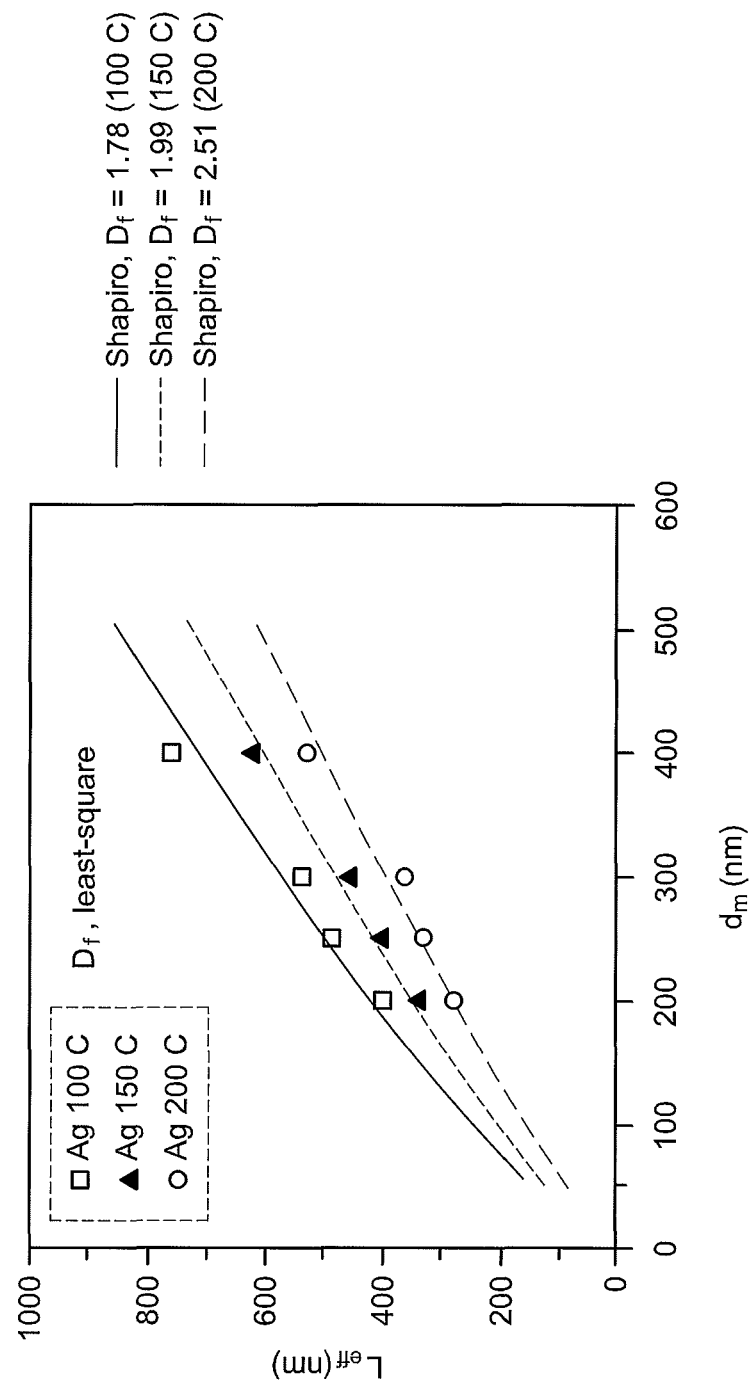
FIG. 6 shows an illustration for use in describing the calculation of the fractal dimension using an exemplary model developed and described herein and experimental filtration results.

An illustration of the technique or method is shown in FIG. 6 (e.g., applied to particles generated using the system of FIG. 3). The symbols represent the effective interception length from experimental filtration results using the Diffusion Battery Screen filter. The curves are the outer diameter of fractal agglomerates computed using the model of Vainshtein and Shapiro (2005). The discrepancy between them is minimized using the least-square method by varying the fractal dimension. The results show that the fractal dimension is 1.78, 1.99, and 2.51 when the sintering temperature in the second furnace is 100, 150 and 200° C., respectively. The fractal dimension obtained here increases with the sintering temperature, which agrees with the fact that sintering at higher temperatures leads to more compact structure. Thus the preliminary results demonstrate that the method can give rise to reasonable fractal dimension measurement.

In addition to the use of the model described in Wang and Pui, Filtration of aerosol particles by elliptical fibers: a numerical study, Journal of Nanoparticle Research 11, 185-196, 2009) and/or the Shapiro model described in Vainshtein and Shapiro described in Vainshtein et al., "Mobility of permeable fractal agglomerates in slip regime," J. Colloid Interface Sci., 284:501-509 (2005), other models may also be used to describe the particles whose morphology is being determined herein. For example, FIGS. 9 and 10 include additional capillary tube models for particle penetration. FIG. 9 provides a capillary tube model 600 described by Spurny et al. in, for example, Spurny, et al., "Aerosol filtration by means of nuclepore filters: Structural and filtration properties," *Environmental Science and Technology* 3, 453-464 (1969). The Spurny capillary tube model (1969) models particle penetration based on impaction deposition on the filter surface, interception on pore opening, and diffusion on tube wall of the pore. FIG. 10 provides a capillary tube model 602 described by Manton in, for example, Manton, M. J., "The impaction of aerosols on a nuclepore filter," *Atmospheric Environment* 12, 1669-1675 (1978); and Manton, M. J., "Brownian diffusion of aerosols to the face of a Nuclepore filter," *Atmospheric Environment* 13, 525-531 (1979). The Manton capillary tube model models particle penetration based on the combined impaction-interception deposition on the filter surface, the diffusion on tube wall of the pore, and diffusion on the filter surface.

Such models may be used and/or modified to define particle penetration through a defined filter. For example, the Spurny model may be modified to take into consideration efficiencies of other models. For example, a modified Spurny model may take into consideration Equations (1), (2), and (3) of the Spurny model of FIG. 9 and Equation (5) of the Manton model in FIG. 10 to define particle penetration through a defined filter. Further, for example, the Manton model may be modified to take into consideration efficiencies of other models. For example, a modified Manton model may take into consideration Equation (2) of the Spurny model of FIG. 9 and Equations (4) and (5) of the Manton model in FIG. 10. One will recognize that any particle penetration model may be of use in defining the correlation of particle penetration described herein with particle morphology of the particles. Still further, for example, the Shapiro model described herein may be modified with a portion of any of the capillary tube models described herein. Further, various models may be more effective at modeling the penetration of certain types of particles through the filter than others. For example, one model may be better at modeling penetration of soot agglomerates through the filter than silver agglomerates, one or more models may be better at modeling penetration of soot spheres through the filter than silver spheres, some models may be better at modeling penetration of agglomerates at one or more face velocities and one or more other models may be better at modeling penetration of agglomerates at one or more other face velocities, etc.

Further, for example, the Kim model is described in Kim et al., "Structural property effect of nanoparticle agglomerates on particle penetration through fibrous filter," *Aerosol Science and Technology* 43, 344-355 (2009) and obtained empirical relations between the maximum particle length and particle mobility diameter for silver nanoparticle agglomerates with open structures and partly sintered structures. The maximum particle length is used to compute the interception efficiency in the Spurny model. The combination of the two models is referred to as Spurny-Kim model (e.g., model used in FIG. 8). As shown in FIG. 8, the Spurny-Kim model agrees well with the experimental filtration results for silver nanoparticle agglomerates when the face velocity is below 7.5 cm/s. Conversely, one can use the filtration results and Spurny-Kim model to determine the maximum length of the testing agglomerates. Further, other empirical or theoretical models can be obtained which include the particle morphological parameters such as the maximum length, fractal dimension, primary particle size, shape factor, etc. and particle density as variables. Such models can be used together with filtration models such as the Spurny model, Manton model, modified Spurny model, etc, to allow determination of one or more particle parameters from the filtration experimental results. Another example is the combined Manton model and Shapiro model which may satisfactorily predict the particle penetration through a Nuclepore® filter when the particle inertia is high. Then, the Manton-Shapiro model may be used to determine the particle fractal dimension from the filtration data. Different combinations of the filtration models and particle models may be formed. Some models may be better at modeling penetration of nanotubes and nanowires, or low fractal dimension particles, or high fractal dimension particles, etc. Some models may be better at modeling penetration for screen filters, or fibrous filters, or multi-micropore filters, etc. Some models may be better at modeling penetration at one for more face velocities, small or large particles, particles with large or small inertias, etc. For example, agglomerates or nanotubes with larger aspect ratios may align with the flow direction when the face velocity is high. A model combining filtration, particle morphological description and the alignment effect may be better at modeling penetration at high face velocities.

The methods and systems described, in each case in one or more of the illustrated embodiments can be used advantageously in different ways. For example, the system may be used for aerosol monitoring in the field of environmental analysis and/or of protection at workplaces or toxicology. Further, for example, the system can also be used alternatively or in addition for aerosol monitoring in the area of process control, wherein a method is used which is based on using at least one aerosol, wherein the device is used to monitor the aerosol. The system can also be used to monitor morphology of liquid-borne nanoparticles manufactured from sol-gel technologies, including metal oxide and metal nitride nanoparticles.

In general, the systems and methods described herein can be used in the area of process monitoring and in the area of process control, in particular in gas phase processes. Examples to be mentioned are the production of carbon nanotubes (CNT), the flame and plasma synthesis (for example of metal oxides and/or mixed oxides), desublimation, hot wall reactors, dispersing and drying methods, gas phase separation processes (chemical vapor deposition (CVD) and/or chemical vapor synthesis (CVS)) or similar processes. In these processes, the methods and systems described herein can be used to carry out process control on the basis of the desired particulate structures (for example, length and diameter of the CNTs, primary particle size and primary particle fraction per agglomerate, fractal dimension, sintered state, agglomerate surface area, agglomerate volume etc.).

The methods and systems described herein can be used to determine a mass concentration of nanoscale gas-borne particles, in particular with respect to future emission and immission limit values of fine dusts. Furthermore, structural parameters of nanoscale particles, in particular the herein-described target variables, can be correlated with the toxic potential, for example for the field of protection at workplaces. This is an advantage in particular in administrations, institutes and specialist sections as well as in the field of inhalation toxicology.

The complete disclosure of the patents, patent documents, and publications cited in the Background, the Summary, the Detailed Description of Exemplary Embodiments, and elsewhere herein are incorporated by reference in their entirety as if each were individually incorporated. Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

What is claimed is:

1. A system for characterizing a totality of particles, comprising:
    a classification apparatus to select a class of the totality of particles having a defined mobility;
    a first particle counter apparatus positioned in a first path of the system for use in determining total particle concentration of the selected class of particles;
    a filter apparatus positioned in a second path of the system, wherein the filter apparatus is defined such that particles of the selected class with different morphologies correspond to different penetration levels therethrough;
    a second particle counter apparatus positioned in the second path for use in determining a filtered particle concentration indicative of particles of the selected class which penetrate the filter apparatus; and
    a calibrator apparatus configured to determine at least one morphological parameter based on the fraction of particles of the selected class penetrating the filter apparatus, the fraction determined as a function of the total particle concentration and the filtered particle concentration, wherein the at least one morphological parameter comprises at least information about the particles of the selected class penetrating the filter apparatus.

2. The system of claim 1, wherein the calibrator apparatus is configured to determine at least one morphological parameter based on a fractional penetration level defined as the ratio of the filtered particle concentration to the total particle concentration.

3. The system of claim 1, wherein the at least one morphological parameter comprises fractal dimension.

4. The system of claim 1, wherein the calibrator apparatus comprises a controller apparatus, and further wherein the controller apparatus comprises at least one processing apparatus for executing instructions of one or more programs to determine at least one morphological parameter based on the fraction of particles of the selected class penetrating the filter apparatus and correlation information, wherein the correlation information comprises at least information correlating different morphologies of particles to different levels of penetration through a defined filter apparatus.

5. The system of claim 4, wherein the correlation information comprises at least information correlating different morphologies of particles to different levels of penetration through a defined filter apparatus at one or more different face velocities.

6. The system of claim 1, wherein the system comprises a line system for guiding a flow of particles, wherein the classification apparatus, the first particle counter apparatus, the filter apparatus, and the second particle counter apparatus are connected in the line system.

7. The system of claim 6, wherein the system further comprises a charge apparatus for charging the totality of particles, wherein the charge apparatus is located upstream of the classification apparatus in the line system.

8. The system of claim 1, wherein each of the first and second particle counter apparatus comprise an electrometer.

9. The system of claim 1, wherein each of the first and second particle counter apparatus comprise a condensation particle counter.

10. The system of claim 1, wherein the filter apparatus comprises at least one of a screen filter, a fibrous filter, a membrane filter, and a multi-micro-pore filter.

11. The system of claim 1, wherein the filter apparatus comprises a multi-micro-pore filter having a pore diameter in the range of 0.005 μm to 100 μm.

12. A method for characterizing a totality of particles, comprising:
    selecting a class of the totality of particles having a defined mobility;
    determining the total particle concentration of the selected class of particles;
    providing a filter apparatus, wherein the filter apparatus is defined such that particles in the selected class with different morphologies have corresponding different penetration levels therethrough;
    filtering the selected class of particles using the filter apparatus and determining a filtered particle concentration indicative of the particles of the selected class which penetrate the filter apparatus; and
    determining at least one morphological parameter based on the fraction of particles of the selected class penetrating the filter apparatus, the fraction determined as a function of the total particle concentration and the filtered particle concentration, wherein the at least one morphological parameter comprises at least information about the particles of the selected class penetrating the filter apparatus.

13. The method of claim 12, wherein determining at least one morphological parameter based on the fraction of particles of the selected class penetrating the filter apparatus comprises:
    determining a fractional penetration level defined as the ratio of the filtered particle concentration to the total particle concentration; and
    determining the at least one morphological parameter based on the fractional penetration level.

14. The method of claim 12, wherein the at least one morphological parameter comprises at least one of fractal dimension and maximum particle length.

15. The method of claim 12, determining the at least one morphological parameter comprises determining the at least one morphological parameter based on the fraction of particles of the selected class penetrating the filter apparatus and correlation information, wherein the correlation information comprises at least information correlating different morphologies of particles to different levels of penetration through a defined filter apparatus.

16. The method of claim 15, wherein the correlation information comprises at least information correlating different morphologies of particles to different levels of penetration through a defined filter apparatus at one or more different face velocities.

17. The method of claim 12, wherein the method further comprises charging the totality of particles prior to selecting the class of particles.

18. The method of claim 12, wherein determining the total particle concentration of the selected class of particles and determining a filtered particle concentration of the selected class comprises using electrometer or a condensation particle counter.

19. The method of claim 12, wherein providing a filter apparatus comprises selecting a filter apparatus based on a pressure drop of the filter apparatus.

20. The method of claim 12, wherein the filter apparatus comprises at least one of a screen filter, a fibrous filter, and a membrane filter.

* * * * *